United States Patent
Gross

(10) Patent No.: US 7,195,888 B2
(45) Date of Patent: Mar. 27, 2007

(54) CALCIUM-INDEPENDENT PHOSPHOLIPASE A2 INDUCES ISCHEMIC VENTRICULAR ARRHYTHMIAS AND DECREASES INFARCTION SIZE

(75) Inventor: Richard W. Gross, Chesterfield, MO (US)

(73) Assignee: Washington University in St. Louis, St. Louis, MO (US)

(*) Notice: Subject to any disclaimer, the term of this patent is extended or adjusted under 35 U.S.C. 154(b) by 484 days.

(21) Appl. No.: 10/737,167

(22) Filed: Dec. 15, 2003

(65) Prior Publication Data

US 2004/0185519 A1  Sep. 23, 2004

Related U.S. Application Data

(60) Provisional application No. 60/455,369, filed on Mar. 17, 2003, provisional application No. 60/433,148, filed on Dec. 13, 2002.

(51) Int. Cl.
*C12Q 1/34* (2006.01)
*C12N 9/16* (2006.01)
*C07H 21/04* (2006.01)

(52) U.S. Cl. .................. 435/18; 435/198; 536/23.2

(58) Field of Classification Search .................. 435/18, 435/198; 536/23.2
See application file for complete search history.

(56) References Cited

U.S. PATENT DOCUMENTS

2005/0003388 A1* 1/2005 Gross et al. .................... 435/6

OTHER PUBLICATIONS

McHowat et al. Am. J Physiol. Jun. 1998, vol. 274, No. 6 Pt 1, pp. C1727-C1737.*
Tang et al. [JBC 272 (13), Mar. 28, 1997, pp. 8567-75].*

* cited by examiner

*Primary Examiner*—Tekchand Saidha
(74) *Attorney, Agent, or Firm*—Armstrong Teasdale LLP

(57) ABSTRACT

A method for evaluating a compound to determine the relative or absolute therapeutic capability of a compound to pharmacologically inhibit ischemia induced activation of iPLA$_2\beta$ in an intact myocardium which comprises treating intact myocardium with a compound, inducing ischemia in the myocardium tissue and determining if there has been a change in expression of iPLA$_2\beta$, its activity or in the iPLA$_2\beta$ regulating network and determining if there has been a change then that the compound is an anti-arrhythmia or myocardial salvage drug.

8 Claims, 12 Drawing Sheets

CALCIUM-INDEPENDENT PHOSPHOLIPASE A2 INDUCES ISCHEMIC VENTRICULAR ARRHYTHMIAS AND DECREASES INFARCTION SIZE

This application claims the benefit of U.S. provisional patent application 60/433,148 filed Dec. 13, 2002 which is incorporated herein by reference in its entirety and the benefit of priority of U.S. provisional patent application 60/455,369 filed Mar. 17, 2003 which is incorporated herein by reference in its entirety.

This invention was made with U.S. government support under National Institute of Health Grant Number 2P01HL5727806A1 and 2RO1HL4125010. The government has certain rights in this invention.

FIELD OF THE INVENTION

This invention relates to phospholipase $A_2$ and more particularly to calcium independent phospholipase(s). More particularly, the invention relates to a method of identifying a drug useful to counteract or treat mammalian malignant ventricular arrhythmia, to reduce infarction size and/or to define the role of iPLA2$_2\beta$ associated endogenous metabolic regulatory compounds (protein, lipids, or metabolic) in the control or modulation of iPLA2$_2\beta$ activity in a living mammal

BACKGROUND OF THE INVENTION

Coronary heart disease (CHD) is the leading cause of death in humans in the U.S. CHD heart disease is so pervasive that more humans die of heart disease than from any other disease. CHD is caused by a narrowing of the coronary arteries that supply blood to the heart. This often results in a heart attack in the victim. Unfortunately, each year about a million Americans have a heart attack and tragically about half or more of these heart attacks are fatal before the heart attack victim can get to a hospital. Heart disease includes congestive heart failure and malignant ventricular arrhythmias. Electrophysiologic dysfunction is believed to be the major cause of death during myocardial infarction in humans[8].

Several Research Publications suggest that activation of myocardial phospholipases during acute cardiac ischemia resulted in the generation of amphiphilic metabolites which alter ion channel function thereby precipitating lethal ventricular dysrhythmias[1-3,9-11]. Since myocytic electrophysiologic function is influenced by the physiochemical properties of the lipids surrounding ion channels[12-13], accelerated hydrolysis of sarcolemmal phospholipid constituents during acute ischemia could potentially provide a foundation for understanding the biochemical basis of ischemia-induced arrhythmias. Additionally, myocardium contains at least three distinct intracellular phospholipase $A_2$ activities encoded on discrete genes (iPLA$_2\beta$, iPLA$_2\gamma$, and cPLA$_2\gamma$)[14,15].

Without being bound by theory, in the early stage of CHD, it is believed that plaque or fatty materials build up inside the walls of human arteries (carrying oxygenated blood) along with blood components which are attracted to the plaque or fatty materials. Sometimes the fatty buildup or plaque breaks open in a human artery which leads to formation of a clot that seals the defect in the artery but unfortunately restricts blood flow. When too little blood reaches the heart, as a result of this restriction in blood flow, the medical condition ischemia or myocardial ischemia results.

In some situations when the ischemia is of a long duration there is generally a resulting heart attack which unfortunately is all too often sometimes fatal. In other situations ischemia disturbs the heart's rhythm inducing an abnormal increasingly disruptive rhythm such as malignant ventricular arrhythmia which is usually destructively fatal.

Arrhythmias include the ventricular and supraventricular type. In the ventricular type the arrhythmias occur in an area in the ventricles typically in or adjacent to the ischemic part. It is believed that arrhythmias in the left ventricle of the heart lead to the most common cause of death due to an ischemic episode from atherosclerosis. These are called ventricular arrhythmias and include ventricular tachycardia, ventricular fibrillation and premature ventricular contractions. Lasting durational ventricular arrhythmias termed malignant ventricular arrhythmia. Malignant ventricular arrhythmia is particularly fatal to humans.

In an effort to combat fatal human heart attacks, medical research strives to identify drugs which are effective against malignant ventricular arrhythmias. However, difficult challenges are presented to that effect in that the process of discovering and developing new pharmaceutical drugs is increasingly expensive and challenging. For example, the average length of time from the discovery of a candidate drug to the time of its US Federal Drug Administration approval has increased. And currently, it is estimated that an average of 10,000 or more lead compounds must be tested in pre-clinical development for every drug that is finally marketed.

Additionally it is estimated that existing pharmaceutical drugs interact with less than five hundred or so biological targets out of an estimated large number of potential targets (~10,000). If this estimate is correct then, this means that the majority of potential drug targets remain undiscovered using presently available techniques.

Thus, despite rapid and noteworthy advances in medical science in this field, a dire need exists for a method of identifying pharmacological drugs which are therapeutic to preventing or ameliorating dangerous and potentially fatal (malignant) ventricular arrhythmias in humans.

DETAILED DESCRIPTION OF THE DRAWINGS

Figure 1A:
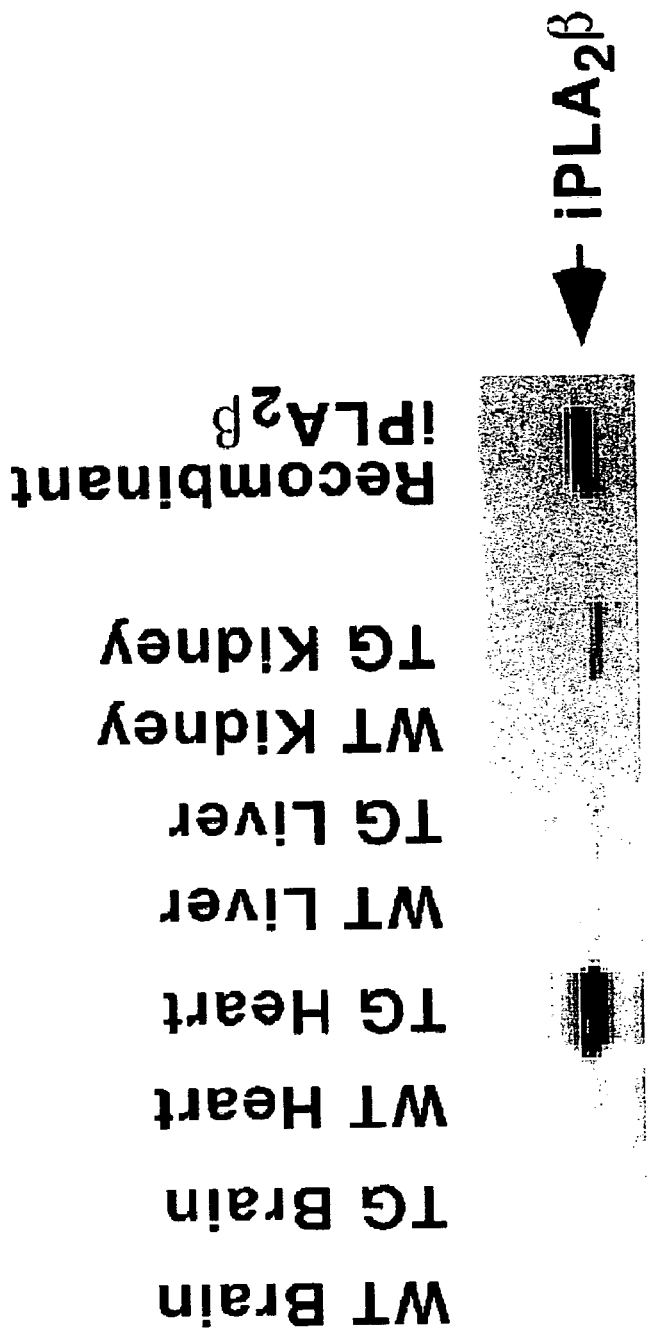
FIG. 1 shows calcium-independent phospholipase $A_2\beta$ (iPLA$_2\beta$) expression in wild-type and transgenic mice.
Figure 1B:
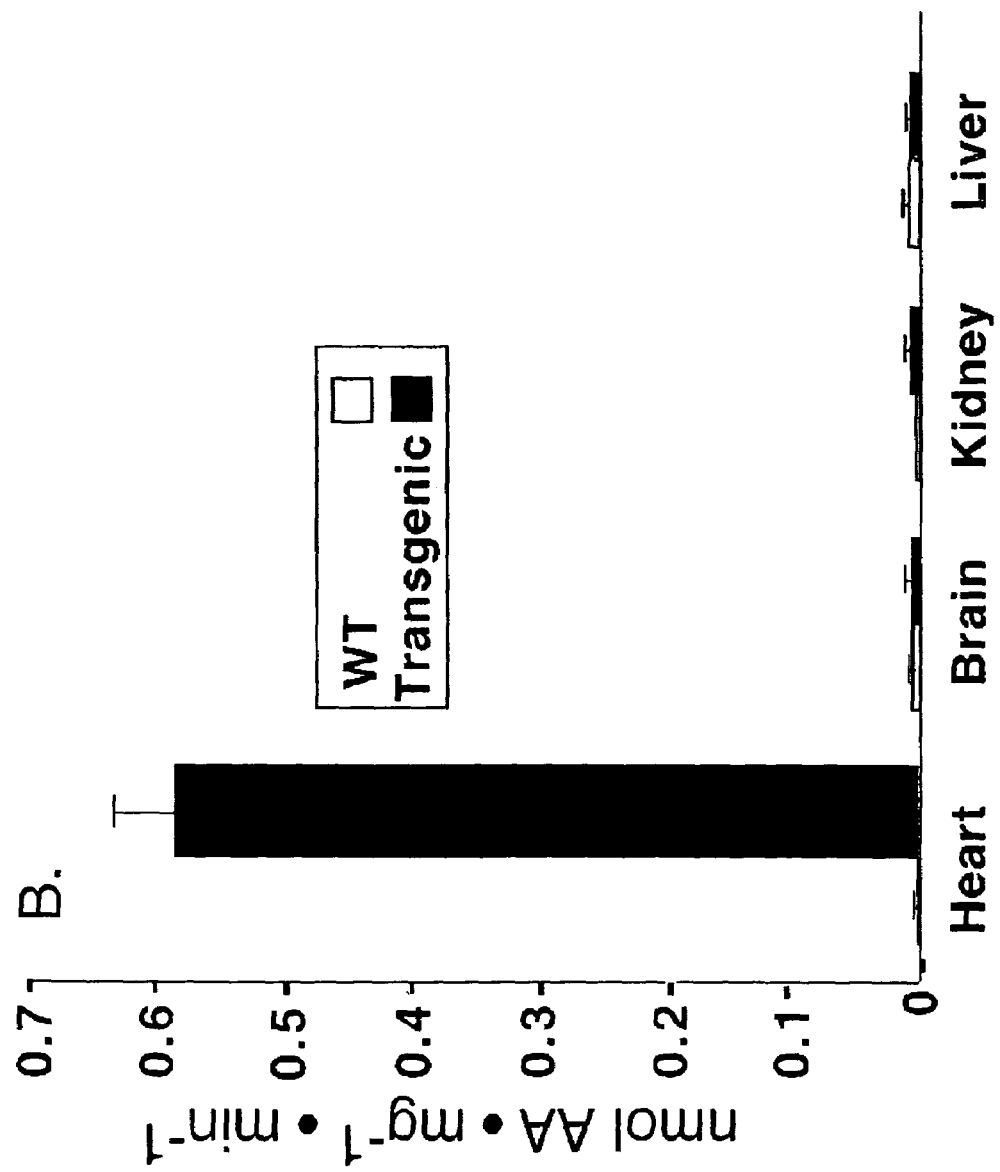

FIG. 1 shows Calcium-independent phospholipase A$_2\beta$ (iPLA$_2\beta$) expression in wild-type and transgenic mice. A, western analysis of iPLA$_2\beta$ expression in cytosol from selected tissues including brain, heart, liver, and kidney from wild-type (WT) and transgenic (TG) mice. Purified recombinant iPLA$_2\beta$ was used as standard. B, iPLA$_2\beta$ activity present in the cytosolic fractions of brain, heart, liver, and kidney of wild-type and TGiPLA$_2\beta$ mice. Phospholipase A$_2$ activity assays were performed by measuring arachidonic acid (AA) released (nmol) per mg/min. as described in the Methods. n=3.

Figure 2A:
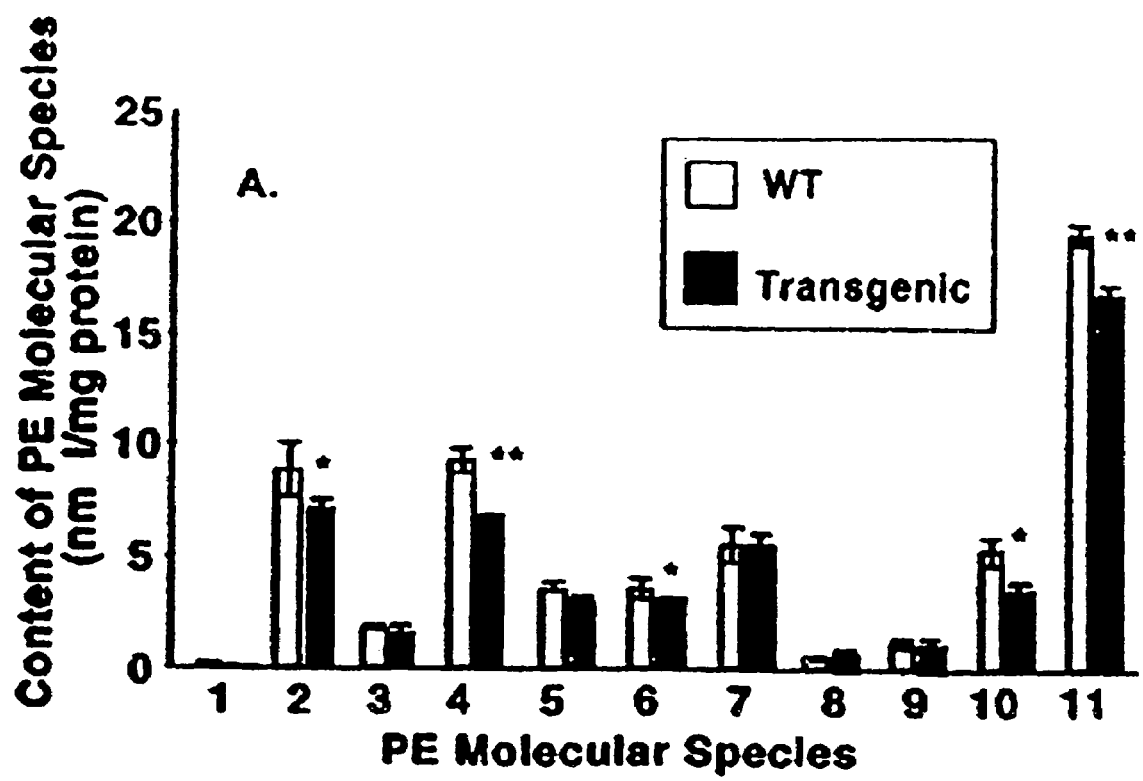
FIG. 2 shows the molecular species distribution from electrospray ionization mass spectra of phospholipids in wild-type and transgenic myocardium.

FIG. 2 shows electrospray ionization mass spectra of phospholipids in wild-type and transgenic myocardium. A, Ethanolamine glycerophospholipid (PE) molecular species in WT (light bars) vs TG iPLA$_2\beta$ (dark bars) myocardium. Individual PE molecular species quantified include: 1, P16:1–20:4; 2., P16:0–22:6; 3, P18:1–20:4; 4, D16:0–22:6; 5, D16:0–22:4; 6, P18:1–22:6; 7, P18:0–22:6; 8, P18:1–22:4; 9, P18:0–22:4; 10, D18:1–22:6; 11, D18:0–22:6 where 'D' and 'P' denote diacyl and plasmenyl subclasses, respectively. *$P<0.01$, **$P<0.001$ (n=3). B, Phosphatidylcholine (PC) molecular species in WT (light bars) vs TG iPLA$_2\beta$ (dark bars) hearts. Individual molecular species quantified include: 1, 16:0–16:0; 2, 16:0–18:2; 3, 16:0–18:1; 4, 16:0–20:4; 5, 18:1–18.1; 6, 18:0–18:1; 7, 16:0–22:6; 8, 16:1–22:4; 9, 18:0–22:6; 11, 18:1–22:4. *$P<0.01$, **$P<0.001$ (n=3). In each case, other molecular species representing <2% of the total pools were also identified without demonstrable differences between control and transgenic mice.

Figure 3A:
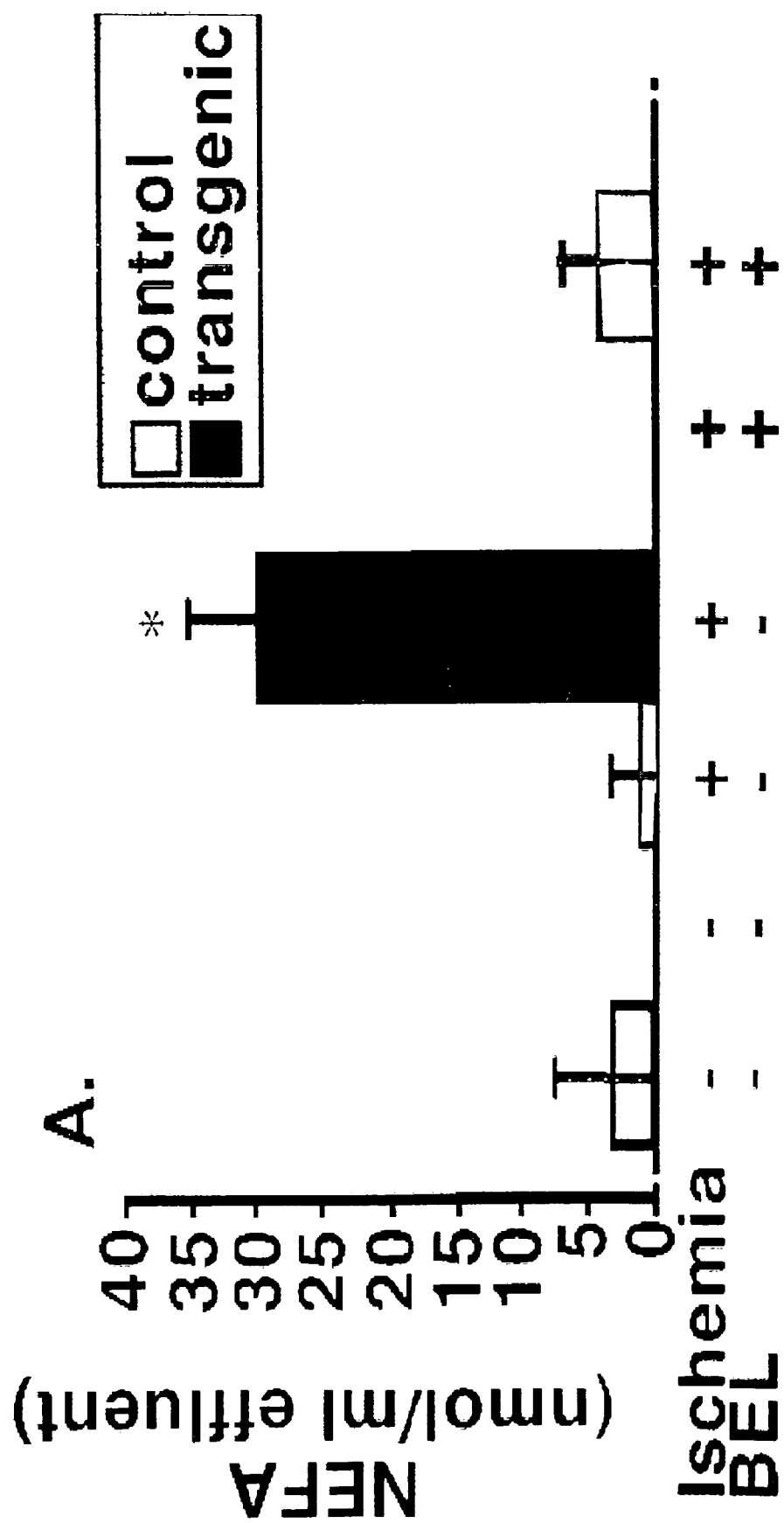
FIG. 3 shows of fatty acid release and lysophosphatidylcholine accumulation in WT and TGiPLA$_2\beta$ Langendorf perfused control and ischemia hearts determinined from electrospray ionization mass spectra.
Figure 3B:
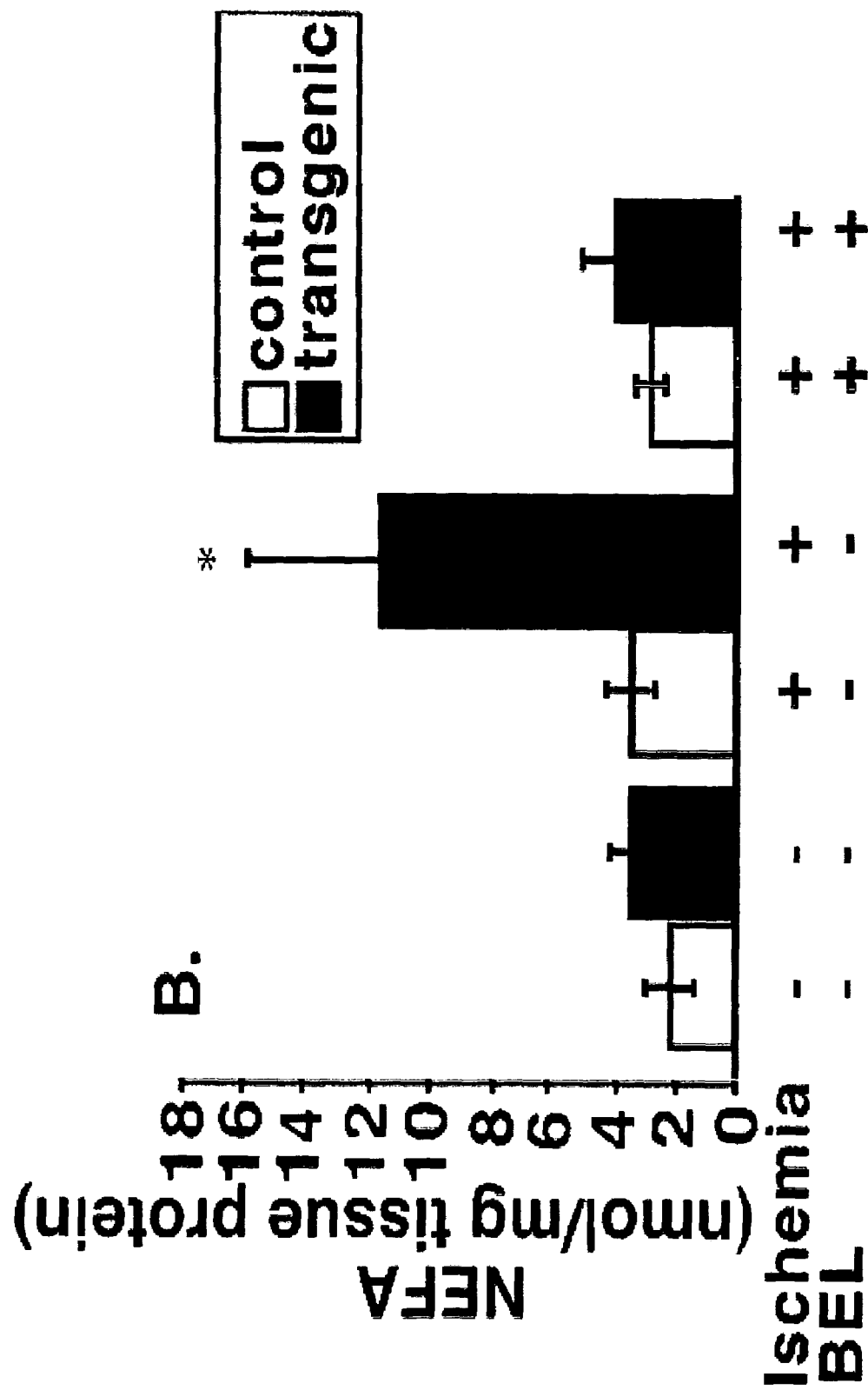
Figure 3C:
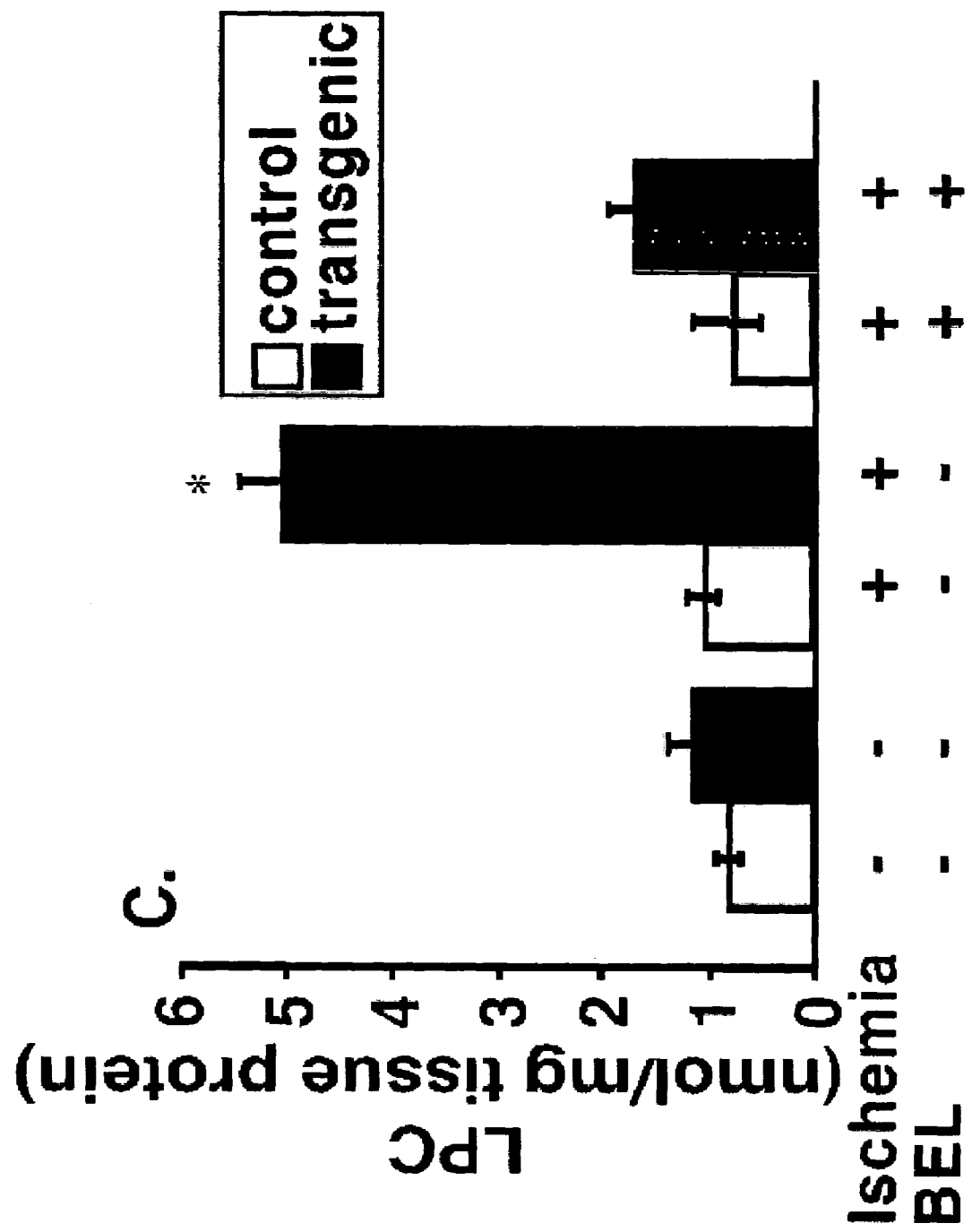

FIG. 3 shows the electrospray ionization mass spectrometric (ESI/MS) determination of fatty acid release into the eluent and in tissues as well as lysophosphatidylcholine accumulation in tissues in WT and TGiPLA$_2\beta$ Langendorf perfused hearts. A, Nonesterified fatty acid (NEFA) release obtained from 15 in of effluent from control or ischemic Langendorf hearts. *$P<0.001$ B, NEFA mass in ischemic heart tissue from WT and TGiPLA$_2\beta$ hearts. *$P<0.01$. C, Lysophosphatidylcholine (LPC) mass in ischemic tissue from WT and TGiPLA$_2\beta$ hearts. *$P<0.0001$. Release of NEFA into the effluents (a) and accumulation of NEFA (b) and LPC (c) in ischemic tissue from Langendorf-perfused hearts [WT (light bars) and TGiPLA$_2\beta$ (dark bars)] were measured in the absence or presence of LAD occlusion (ischemia) in the absence (−) or presence (−) of BEL pretreatment as indicated.

Figure 4A:
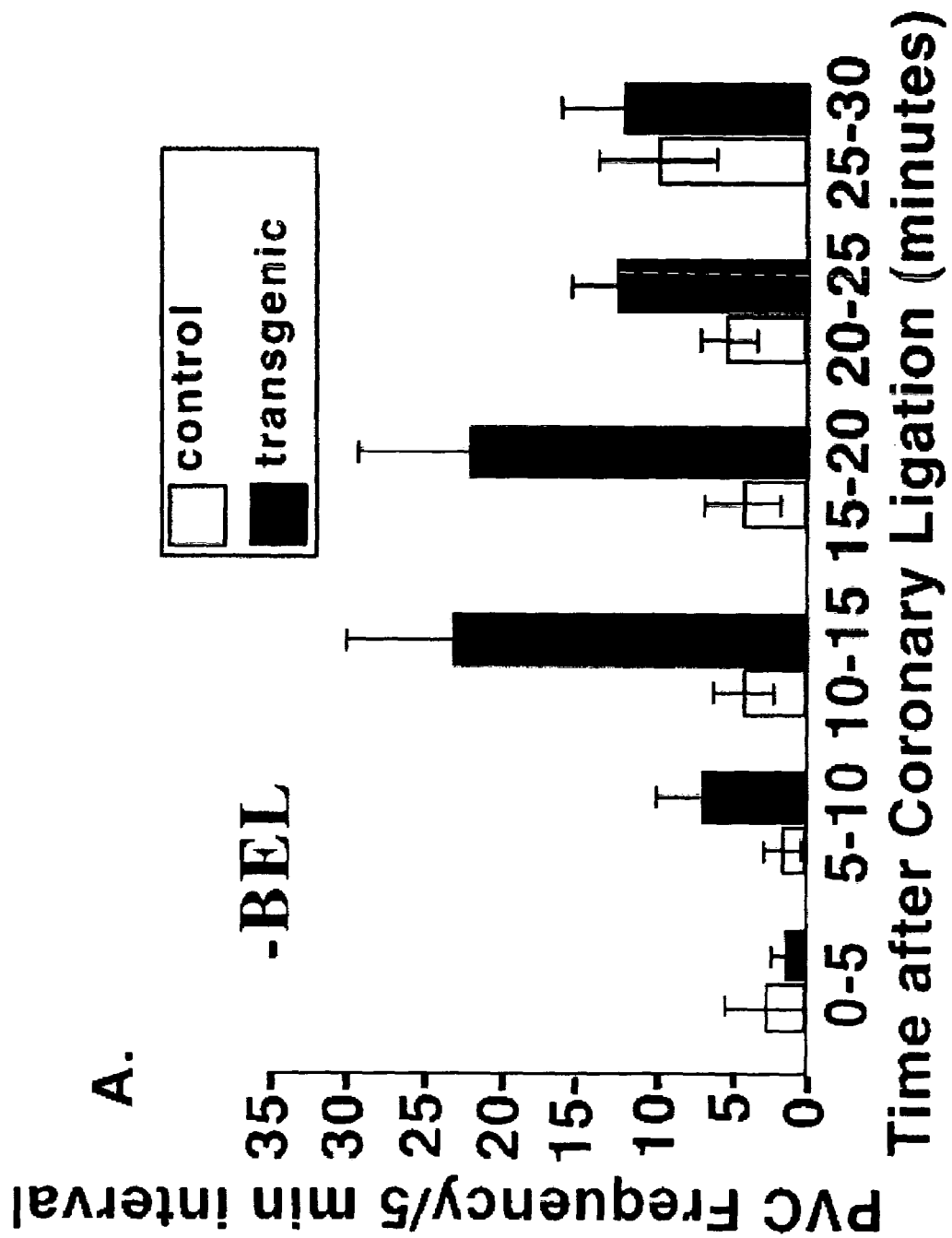
FIG. 4 shows premature ventricular contraction frequency and Total Episodes of Ventricular Tachycardia or TGiPLA$_2\beta$ hearts (dark bars) in the absence or presence of LAD occlusion [in control (open bars)] in the absence (−) or presence (+) of BEL pretreatment as indicated.

FIG. 4 shows Premature ventricular contractions (PVCs) and ventricular tachycardia (VT) after coronary ligation in the presence and absence of BEL in wild-type and iPLA$_2\beta$ transgenic Langendorf-perfused mouse hearts. Data are presented as the +/− standard deviation. A, frequency of PVCs in wild type control mouse hearts (open bars, n=19) and in TGiPLA$_2\beta$ transgenic mouse hearts (closed bars, n=24) in the absence of BEL pretreatment (−BEL). Total PVCs were recorded in 5 minute intervals (0–5, 5–10, 10–15, 15–20, 20–25, and 25–30 min) after ligation of the LAD coronary artery in TGiPLA$_2\beta$ and wild-type control Langendorf hearts. The mean PVC frequency per interval (PVC frequency/5 min interval) was then plotted vs time interval after coronary ligation. Repeated measures ANOVA showed a significant difference between the PVC frequencies for wild type controls and TGiPLA$_2\beta$ mice (p=0.0003). B, The effect of BEL pretreatment (+BEL) on PVC frequency measured in 5 min intervals after coronary litigation. Repeated measures ANOVA showed a significant decrease in PVC frequency/5 min interval for BEL-treated TGiPLA$_2\beta$ hearts (p=0.0002 comparing TGiPLA$_2\beta$ with vs without BEL pretreatment, n=10). Similarly, BEL pretreatment reduced PVC frequency in WT hearts (p=0.03 comparing WT with and without BEL pretreatment, n=8). C, Frequency histogram showing total episodes of VT in TGiPLA$_2\beta$ transgenics (closed bars, n=24) vs wild-type control hearts (open bars, n=19) with (+) and without (−) BEL pretreatment. BEL pre-treatment resulted in a significant reduction of VT episodes in transgenic hearts as determined by ANOVA (p=0.002).

Figure 5:
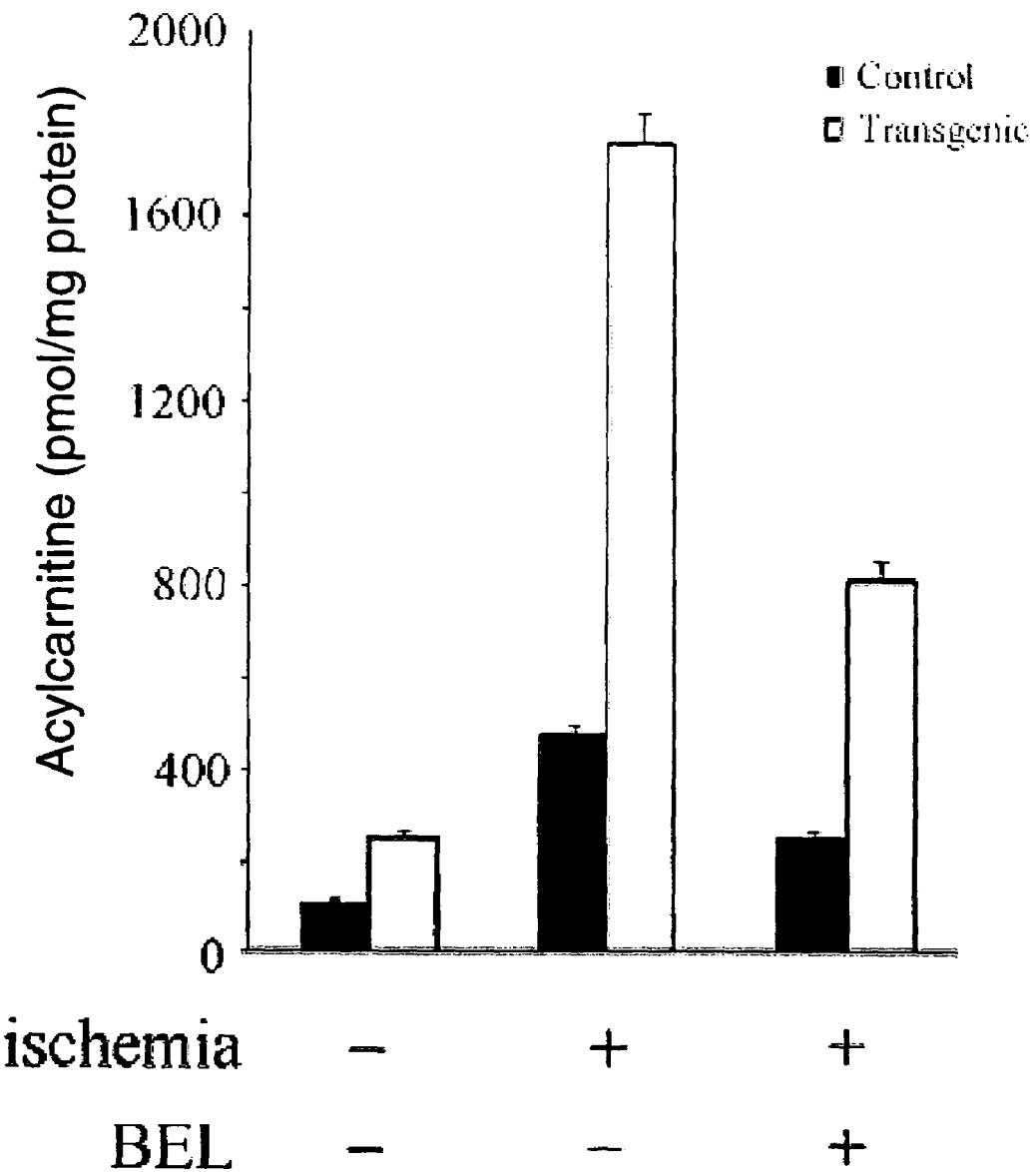
FIG. 5 shows acylcarnitine formation during control and ischemic conditions in wild type or iPLA$_2\beta$ transgenic hearts. The results show that phospholipase activity is necessary for the production of a major portion of acylcarnitines synthesized during myocardial ischemia. The ischemia-induced increase in acylcarnitines in wild type mice is inhibited by BEL. Moreover, iPLA$_2\beta$ transgenic mice sustain a dramatic increase in acylcarnitine content during myocardial ischemia in comparison to wild type mice. Moreover, this increase is also inhibited by BEL. Collectively, these results demonstrate the importance of iPLA$_2\beta$ in the synthesis of a major portion of acylcarnitines produced during ischemia.

FIG. 5 shows measurement of acylcarnitines in control or transgenic mice expressing iPLA$_2\beta$ perfused in the Langendorf mode at normal flow for 5 min prior to perfusion with BEL (10 uM) for 5 min or vehicle alone. Next, ischemia was induced by ligating a marginal branch of the LAD coronary artery and ischemia was induced for 15 minutes. Aliquots of the ischemic zone were taken and rapidly frozen. After addition of internal standard, aliquots of frozen tissue were extracted and analyzed for acylcarnitine content by ESI mass spectrometry by comparisons to standard utilizing methods previously described.

Figure 6:
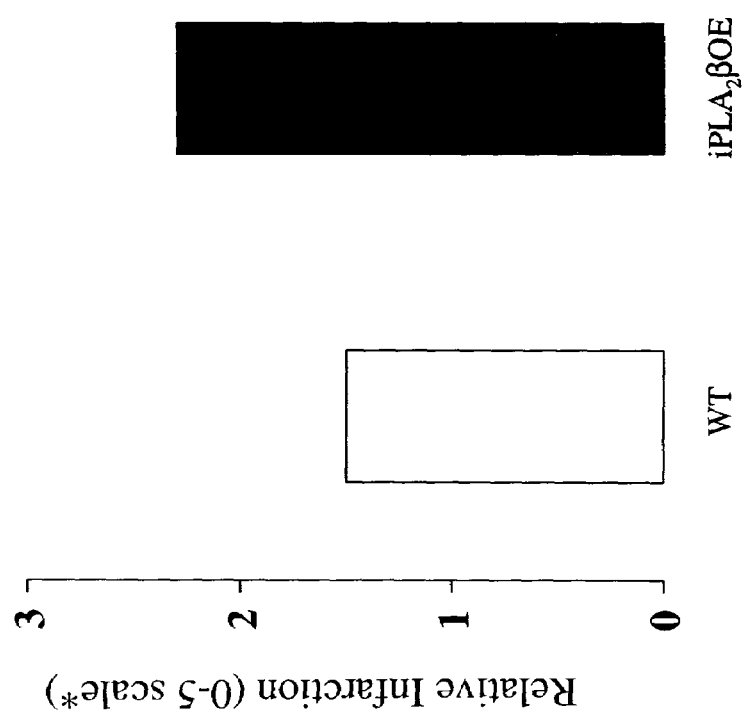
FIG. 6 shows data that demonstrate that mice which express iPLA$_2\beta$ undergo greater damage during ischemic insult in comparison to wild type mice. These results underscore the importance of minimizing the functional activation of iPLA$_2\beta$ during myocardia ischemia to maximize the salvage of jeopardized regions of ischemic myocardium.

FIG. 6 shows increased ischemic damage in iPLA$_2\beta$ transgenic mice. Control or iPLA$_2\beta$ transgenic mice were perfused retrograde through the aorta for an equilibration interval prior to the induction of ischemia by ligating the LAD coronary artery. After 15 min. of ischemia the tissue was fixed and the magnitude of infarcted tissue was assessed on a 1 to 5 scale. The results demonstrate mice expressing iPLA$_2\beta$ sustained greater injury than WT mice identifying iPLA$_2\beta$ as a therapeutic target for treatment of ischemic injury.

BRIEF DESCRIPTION OF THE INVENTION

In a first embodiment, a method for evaluating a compound comprises determining the relative or absolute therapeutic capability of that compound to pharmacologically effectively inhibit-ischemia induced activation of iPLA$_2\beta$ in intact myocardia. In an aspect, the library comprises at least two, three to a multiplicity of compounds.

In an aspect, a screening method comprises treating an intact myocardia(um) capable of expressing iPLA$_2\beta$ with a compound, intentionally inducing ischemia in myocardial tissue and determining the level of expression of iPLA$_2\beta$ activity or any measurable parameter of iPLA$_2\beta$ activity which gives an indication of the administration of the compound having or having had an effect of the level of iPLA$_2\beta$ expression or iPLA$_2\beta$ activity.

In a further aspect, the invention comprises analyzing for the presence of fatty acids in myocardial tissue or in the eluate from ischemic zones either in situ or in an isolated perfused heart preparation (as a standard abnormal object model of heart disease) following induction of ischemia, determining if fatty acids are present (or notably increased following an induction of ischemia in a nontreated myocardium tissue) and determining that the compound is an inhibitor of iPLA$_2\beta$ activity or activity of the regulatory complex (i.e., therapeutic target for drugs against ventricular arrhythmia).

In a further aspect thereof, the expression of iPLA$_2\beta$ activity is evaluated in such analysis, by mass and by enzymatic activity (e.g. as assessed by FA release into the venous effluent, and or lysolipid production or acylcarnitine formation) in an intact organ setting, or in another use from cardiac myocytes or cells thereof since iPLA$_2\beta$ activity is tonically inhibited by calmodulin and/or other natural system regulatory proteins or regulatory elements (FA=fatty acid).

In an aspect, a method of treating a patient comprises administering a pharmacologically effective amount of an anti-arrhythmic drug effective to against the expression of iPLA$_2\beta$ activity to a patient to ameliorate at least one of sudden death, ischemic damage, embolism and clot, aneuryisms and relief of intolerable symptoms of the patient such as, at least one of, pain, dizziness or other clinical symptoms of ischemia. In an aspect, the patient is a living mammal such as a living mammal or tissue representative of a living animal or of a living mouse.

In an aspect, the invention comprises an animal model and a method of testing an animal model further comprising administering a drug to a perfused beating heart tissue thereby intermittently inducing ischemia to the heart tissue and measuring the heart tissue or venous effluent (e.g., coronary sinus in situ) for a change in composition after an adequate time has passed following administration of the drug to the tissue.

In an aspect an animal model is prepared which replicates the condition of malignant ventricular arrhythmia in a living human or will so replicate. As a result of determining a therapy for such an animal model a translation is made to provide a therapy for a human or other living mammal. In an aspect the animal model is transgenic in whole or part.

In an aspect an animal model is a functionally capable model comprising living cells comprising matter which has been genetically altered to produce at least one of a transgenic, knockout and knockdown cellular system in the model, having functional capability to express iPLA$_2\beta$ in an amount detectable. In a further aspect thereof the cells contain recombinant material including a promoter and sequencing instructions so as to adequately encode and express iPLA$_2\beta$ (as a target protein) and its regulatory complex for the discovery of anti-arrhythmia drugs or anti-ischemic damage drugs.

In an aspect, an animal model having living recombinant cells present iPLA$_2\beta$ as a target for the discovery of anti-arrhythmia drugs comprises recombinant matter which produces a bio-system having the functional capability to express iPLA$_2\beta$ in an amount detectable by instrumental detection means. In a further aspect the living cells has as a target iPLA$_2\beta$. It is understood that the compositions of the animal model are selected such to provide a functional animal model replicate of an animal having iPLA$_2\beta$ expression capability and expression functionality interactions with its regulatory complex and that the conditions, parameters of functional operation of the animal model are such that the utility of this animal model provides iPLA$_2\beta$ as a target for the discovery and identification of pharmacologically effective pharmacogically suitable drugs. In an aspect, the model is a functional mouse.

In an aspect a method of therapy for a patient comprises effective administering a pharmacologically effective amount of an anti-iPLA$_2\beta$ expression drug or anti-iPLA$_2\beta$ activity drug to a patient at risk for or having sustained malignant ventricular arrhythmia.

In an aspect, therapy to be provided by an identified compound comprises preventing death or to relieve one or more intolerable symptoms or to successfully terminate a malignant ventricular arrhythmia in a mammal for preserving the life of the victim. In an aspect, a therapeutic treatment would be brought about by preventing an arrhythmia, particularly, malignant ventricular arrhythmia, or converting a non-tolerated arrhythmia to a tolerable arrhythmia or eliminating an arrhythmia but keeping the patient viable, or by reducing infarct size or by preventing aneuryism formation.

In an aspect, a method of practicing medicine utilizing metabolic activity comprises effectively administering a pharmacologically effective amount of an anti-iPLA$_2\beta$ expression drug or anti-iPLA$_2\beta$ activity drug in the natural setting of its regulatory components to a patient at risk for or having sustained malignant ventricular arrhythmia.

In an aspect, a medicinal management system comprises administering a pharmacologically effective amount of an anti-arrhythmia drug which inhibits the expression of either iPLA$_2\beta$ mass or prevents expression of its activity in a patient.

In an aspect, a method of drug discovery/screening/assaying in clinical diagnosis management system comprises administering a drug to an animal model, intentionally inducing ischemia in the animal model, measuring the amount or concentration of a compound which is indicative of activity of the drug upon expression of iPLA$_2\beta$ activity and determining that said drug is an effective anti-arrhythmia drug when said activity effect is determined to be positive.

In an aspect, a pharmaceutical composition comprises a drug which inhibits the expression iPLA$_2\beta$ activity by preventing ischemia-induced release of tonic inhibition in an animal model system replicate of a living animal.

In an aspect, a pharmaceutical kit comprises a container housing a pharmaceutical composition comprising a drug which inhibits the expression iPLA$_2\beta$ activity in an animal model system replicate of a living animal.

In an aspect, a determination is made that a drug is an anti-arrhythmic drug when after a drug is administered to an animal capable of expressing iPLA$_2\beta$ activity is reduced following ischemia induction in the model.

In an aspect, a high through-put primary screen is employed using mass spectrometric methodology or as a secondary screen to identify compounds which modulate the iPLA$_2\beta$-calmodulin interaction found in a naturally occurring biologic situation. iPLA$_2$ in myocardium is tonically inactive, being activated only after the onset of the ischemic stimuli (or other stimuli which predispose to arrhythmias such as fasting, hormone release etc.). Thus, it is not the amount of iPLA$_2$ mass that is important, but the amount of activity that is released from its tonic inhibition by association from calmodulin and/or other regulatory elements.

In an aspect, using this to identify agents which modulate the interaction of iPLA$_2\beta$ with its regulatory elements for treatment of other disease (e.g. diabetes through increasing insulin release) using this as a model test system for candidate drugs.

In an aspect, the induction is carried out in an intact animal model. In an aspect, the model is a perfused, isolated and living tissue such as heart tissue or a representative sample thereof or a cell system representative thereof.

In an aspect, the method to test an animal model comprises testing for the release of FFA into the venous effluent from the model after introduction of evaluation compound into the perfused site.

In an aspect, the inventor measures at least one of the amount of moieties such as at least one of free fatty acid, acylcarnitine, lysolipid and ceramide in a living system and isolated perfused heart during control or ischemic conditions and if the amount of at least one of these moieties is the greater, the same as, substantially changed or lesser than the compounding normal amount of a drug, the inventor determines that the tonic of iPLA$_2$β inhibition is modified i.e. and my drug is a drug which is a potential anti-arrhythmia drug or an agent which decreases infarction size or aneuryism formation.

In an aspect, the inventor can measure or determine the molar or weight ratio of one compound of the living animal model to another and if the ratio is greater than control less than or equal to ischemic values. The inventor can determine that the test compound is a drug which is an anti-arrhythmia drug. The normal amount or concentration is measured in the perfused heart intact animal model and compared to that in the ischemic heart in the absence or presence of the compound to be tested. For each component which is measured using the animal mode, the inventor can use mass spectrometry or other standard radiometric, fluorometric, immunoassay, gas chromatography or coupled enzyme assay systems as described previously in the art.

In an aspect the invention comprises analyzing for the presence of fatty acids in the myocardium tissue or venous effluents following intentional induction of ischemia in a perfused heart iPLA$_2$β transgenic model. If the fatty acids are absent (or notably reduced following an induction of ischemia in a nontreated myocardium tissue) one can make a determination that the compound is an inhibitor of iPLA$_2$β catalytic regulatory network and identify a potential therapeutic drug against malignant ventricular arrhythmia. In an aspect, the drug may be advanced in a drug screen based on its aforedescribed inhibition of iPLA$_2$β alone, or in the presence of calmodulin and other regulatory proteins.

In an aspect, the invention comprises making a determination that the compound inhibited the ischemia induced activation of iPLA$_2$β, in an isolated perfused heart model and using ESI/MS to quantify the release of fatty acids into the effluent and measuring the accumulation of fatty acids and lysolipids in ischemic zones of the heart model.

In an aspect, a determination is made as to whether a drug is an effective anti-arrhythmic drug based on whether the drug administered to the animal model capable of expressing iPLA$_2$β, produced a suppression of an arrhythmia and/or reduction in size of the infarction and/or reduction in an aneuryism.

In an aspect, a method of treating a patient comprises administering an effective amount of an anti-arrhythmia drug to the patient whereby the size of the infarction is reduced and the aneuryism formation is reduced.

DETAILED DESCRIPTION OF THE INVENTION

The inventor has discovered a cause and effect relationship between ischemia-induced phospholipolysis by iPLA$_2$β and malignant ventricular arrhythmias and for the first time identified iPLA$_2$β as the phospholipase A$_2$ activated during cardiac ischemia.

The inventor has discovered an enhanced effective method for screening a compound for its efficacy against sustained ventricular arrhythmia and for a method to identify and rank compounds such as members of a library that have potential as inhibitor(s) to sustained ventricular arrhythmias. Methods are also disclosed herein for screening components of a compound library to be screened to determine if any members of the library which have a higher therapeutic capability relative to a pre-selected indicator compound acting as a standard in relation to anti-ventricular arrhythmia.

This discovery has utility as a method of drug discovery in the areas of at least discovery of effective inhibitors to iPLA2Beta expression, regulators of endemic activity, rescue drugs, counteractants to malignant ventricular arrhythmias and inhibitors, blockers to malignant ventricular arrhythmias by virtue of the discovery by the inventor and presentation herein for the first time of iPLA2Beta as the target for the discovery of such inhibitors, blockers, regulators, counteractants, and rescue drugs. Further utility is provided as an animal model useful in screening drugs as recited above and in evaluating treatments for patients afflicted with undesirable malignant ventricular arrhythmias. In a further aspect the discovery herein presents a method to identify such effective inhibitors, counteractants, rescue drugs and blockers absent adverse side effects to the recipient patient for such drugs and to determine therefrom whether such drugs are therapeutic. In an aspect the inhibitor is a to prophalax to the patient against malignant ventricular arrhythmias. In an further aspect, an analysis and determination is made on the basis of effects of drugs on the biosystem including iPLA2Beta and its natural regulants.

As used herein, the term "arrhythmia" means an abnormal heartbeat that may be unusually fast or unusually slow. While an occasional skipped heartbeat is not normally cause for alarm, serious arrhythmia is cause for great alarm as it is life threatening especially if not medically adequately treated in a short time. A malignant ventricular arrhythmia is considered a life threatening event while a non-sustained ventricular arrhythmia is not considered life threatening unless it reoccurs with some frequency or in groups. However, malignant ventricular arrhythmia is a life threatening medical emergency. A tachyarrhythmia is a form of ventricular arrhythmia when the heart is beating at an abnormally high rate and can lead to or be an indicator of a risk of sudden death.

As used herein, the term "compound" includes cell(s), compounds, ions/anions, cations and salts.

As used herein, the term "tissue" includes tissue, cells and collections of a multiplicity of cell lines or a sample thereof or a sample representative thereof. In an aspect the tissue is representative of a living biological system such as a living mammalian tissue such as in a tissue culture or living mammal or in a living transgenic mouse.

As used herein, the term "peptide" is any of a group of compounds comprising two or more amino acids linked by chemical bonding between their respective carboxyl and amino groups. The term "peptide" includes peptides and proteins that are of sufficient length and composition to effect a biological response, e.g. antibody production or cytokine activity whether or not the peptide is a hapten. term "peptide" includes modified amino acids, such modifications including, but not limited to, phosphorylation, glycosylation, acylation prenylation, lipidization and methylation.

As used herein, the term "polypeptide" is any of a group of natural or synthetic polymers made up of amino acids chemically linked together such as peptides linked together. The term "polypeptide" includes peptide, translated nucleic acid and fragments thereof.

As used herein, the term "polynucleotide" includes nucleotide sequences and partial sequences, DNA, cDNA, RNA variant isoforms, splice variants, allelic variants and fragments thereof.

As used herein, the terms "protein", "polypeptide" and "peptide" are used interchangeably herein when referring to a translated nucleic acid (e.g. a gene product). The term "polypeptide" includes proteins.

As used herein, the term "isolated polypeptide" includes a polypeptide essentially and substantially free from contaminating cellular components.

As used herein, the term "isolated protein" includes a protein that is essentially free from contamination cellular components normally associated with the protein in nature.

As used herein, the term "nucleic acid" refers to oligonucleotides or polynucleotides such as deoxyribonucleic acid (DNA) and ribonucleic acid (RNA) as well as analogs of either RNA or DNA, for example made from nucleotide analogs any of which are in single or double stranded form.

As used herein, the term "patient" and subject" are synonymous and are used interchangeably herein.

As used herein, the term "expression" includes the biosynthesis of a product as an expression product from a gene such as the transcription of a structural gene into mRNA and the translation of mRNA into at least one peptide or at least one polypeptide.

As used herein, the term "mammal" includes living animals including humans and non-human animals such as murine, porcine, canine and feline.

As used herein, the term "sample" means a viable sample of biological tissue or fluid and is not limited to heart tissue. Biological samples may include representative sections of living tissues.

The phrase "a sequence encoding a gene product" refers to a nucleic acid that contains sequence information, e.g., for a structural RNA such as rRNA, a tRNA, the primary amino acid sequence of a specific protein or peptide, a binding site for a transacting regulatory agent, an antisense RNA or a ribozyme. This phrase specifically encompasses degenerate codons (i.e., different codons which encode a single amino acid) of the native sequence or sequences which may be introduced to conform with codon preference in a specific host cell.

By "host cell" is meant a cell which contains an expression vector and supports the replication or expression of the expression vector. Host cells may be prokaryotic cells such as *E. coli*, or eukaryotic cells such as yeast, insect, amphibian, e.g. Xenopus, or mammalian cells such as HEK293, CHO, HeLa and the like.

As used herein a "therapeutic amount" is an amount of a moiety such as a drug or compound which produces a desired or detectable therapeutic effect on or in a mammal administered with the moiety.

The term "recombinant" when used with reference to a cell, or protein, nucleic acid, or vector, includes reference to a cell, protein, or nucleic acid, or vector, that has been modified by the introduction of a heterologous nucleic acid, the alteration of a native nucleic acid to a form not native to that cell, or that the cell is derived from a cell so modified. Thus, for example, recombinant cells express genes and proteins that are not found within the native (non-recombinant) forms of the cell or express native genes that are otherwise abnormally expressed, under expressed or not expressed at all.

An "expression vector" is a nucleic acid construct, generated recombinantly or synthetically, with a series of specific nucleic acid elements which permit transcription of a particular nucleic acid in a host cell. The expression vector can be part of a plasmid, virus, or nucleic acid fragment. Typically, the expression vector includes a nucleic acid to be transcribed operably linked to a promoter.

In an aspect the invention comprises a method of therapy for a patient which comprises effective administering a pharmacologically effective amount of an anti-iPLA$_2\beta$ expression drug or anti-iPLA$_2\beta$ activity drug to a patient at risk for malignant ventricular arrhythmia.

Generally, an arrhythmia is clinically detectable from an electrocardiogram when the output shows a depolarization wave which is spreading through the ventricles along with other clinically defined parameter abnormalities. ECG as the T wave has unusual morphology and beats are generally below 120 beats per minute.

In an aspect, a method of practicing medicine by effectively assessing enzymatic activity of iPLA$_2\beta$ in it's natural setting comprises effectively administering a pharmacologically effective amount of an anti-iPLA$_2\beta$ expression drug or anti iPLA$_2$ activity drug in the natural setting of its regulatory components to a patient at risk for malignant ventricular arrhythmia.

In an aspect, a method is provided herein to identify biologic or pharmacologic effectors which modulate the iPLA$_2\beta$ regulatory network in intact mammalian hearts In an aspect, if the compound is a biologic naturally occurring compound (e.g. lipids, peptides or nucleotides (e.g. ATP, cAMP)) then the enzymes which make these compounds represent a new pharmaceutical enzyme targets therefore are identified by this method.

In an aspect, a medicinal management system comprises administering a pharmacologically effective amount of an anti-arrhythmia drug which inhibits the expression of iPLA$_2\beta$ mass or activity to a patient.

In an aspect, a clinical diagnosis management system comprises administering a drug to an animal model, intentionally inducting ischemia in the animal model, measuring the amount or concentration of a compound which is indicative of activity of the drug upon expression of iPLA$_2\beta$ and determining that said drug is an effective anti-arrhythmia drug when said activity effect is positive (effective dose).

In an aspect, a pharmaceutical composition comprises a drug which inhibits the expression of iPLA$_2\beta$ activity by preventing ischemia-induced release of tonic inhibition in an animal model system replicate of a living animal.

In an aspect, this invention uses a mouse model capable of expressing iPLA$_2\beta$ and having genetically crossed systems so as to study, create and determine the effects of other proteins in genetically engineered mice on ischemia induced arrhythmias.

In an aspect, the invention comprises a pharmaceutical kit comprising a container having a pharmaceutical composition comprising a drug which inhibits the expression iPLA$_2\beta$ activity in an animal model system replicate of a living animal.

In an aspect, therapy to be provided by an identified compound comprises preventing death or relieving one or more intolerable symptoms of arrhythmia or to successfully terminate a malignant ventricular arrhythmia in a mammal thereby preserving the life of the victim. In an aspect, a therapeutic treatment would be brought about by preventing an arrhythmia, particularly, malignant ventricular arrhythmia, or converting a non-tolerated arrhythmia to a tolerable arrhythmia or eliminating an arrhythmia but keeping the patient alive and hopefully viable.

Normally, heart attacks start with angina and normally patients are not in a hospital when such angina occurs. As regards to the latter, it would be enormously beneficial if a drug could be identified which could be effectively administered to a patient undergoing angina so that the patient's chances of survival are increased and that the patient has a better chance of making it to a hospital alive. Further, in an aspect of the invention, a drug identified by this invention could be administered chemically to a patient so as to prevent arrhythmia or limit it as recited above to somehow allow the patient to remain in a sustained healthy condition during transport to a hospital where in depth treatment to counter malignant ventricular arrhythmia can be had.

Due to its relative ease of genetic manipulation, the mouse has become the prototypic animal model for validation of hypotheses implicating specific proteins in whole organ pathophysiologic processes. The inventor has demonstrated that murine myocardium possessed extremely low levels of iPLA$_2$β activity and other researchers have reported that malignant ventricular tachyarrhythmias are infrequent during murine acute cardiac ischemia[6,7]. To determine if the diminutive amounts of cardiac phospholipase A$_2$ activity in murine myocardium and the paucity of ischemia-induced malignant tachyarrhythmias in the mouse were serendipitous findings, or represented a natural species-specific knockout of an important human pathophysiologic phenotype, the inventor expressed iPLA$_2$β transgenically in murine cardiac myocytes by exploiting the cardiac myocyte selectivity of the αMHC promoter[16].

The function of complex biological organisms relies on the meticulous control of cellular activity, including close regulation of cell growth, proliferation and function. The family of enzymes known as the phospholipases A$_2$ has been implicated in the control of cellular activity by catalyzing the esterolytic cleavage of fatty acids from phospholipids, thereby regulating the release of lipid second messengers, cellular growth factors, and the properties of the cellular membrane (Samuelsson et al., Annu. Rev. Biochem. 47:997–1029, 1978; Moolenaar, W. H., Curr. Opin. Cell. Biol. 7:203–10, 1995). In particular, by controlling the production of second messengers such as arachidonic acid and its biologically active eicosanoid metabolites, the phosopholipases A$_2$ are involved in modulating such processes as cellular growth programs, inflammation, vascular tone and ion channel function. (Needleman et al., Annu. Rev. Biochem. 55:69–102, 1986).

However, the phospholipases A$_2$ are a broad family of enzymes with varying kinetic and physical properties, and distinct functions. Early research focused on distinguishing broad classes of the enzymes within the larger family. Several classes were distinguished using in vitro activity assays, and are categorized based on the dependence of their enzymatic activity on the presence of calcium ion. (See e.g., Demel et al, Biochim. Biopliys. Acta 406:97–107,1975). Thus, one class, the secretory phospholipases A$_2$ are distinguished by an obligatory dependence on high (millimolar) concentrations of calcium ions, as well as low molecular weights (14–18 kDa) and relative heat stability. (Demel et al., supra; Tischfield, J. A., J. Biol. Chem. 272:17247–50, 1997). The activity of a second class, the calcium-facilitated phospholipases A$_2$ is facilitated by the presence of nanomolar concentrations of calcium ions, but the presence of the calcium ion is not obligatory. (Loeb et al., J. Biol. Chem. 261:10467–70, 1986; Kramer et al., Biochim. Biophys. Acta 878:394–403; Glover et al., J. Biol. Chem. 270:15359–67, 1986). A third class of enzymes is entirely calcium-independent in vitro studies, and is also distinguished by a finely tuned inhibition by (E)-6-(bromomethylene)-3-(1-napthalenyl)-2H-tetrahydropyran-2-one (BEL). (Wolf et al., J. Biol. Chem. 260:7295–303; Hirashima et al., J. Neurochem. 59:708–14; Lehman et al., J. Biol. Chem. 268:20713–16).

U.S. Pat. No. 5,589,170 which issued to Simon Jones et al on Dec. 31, 1996 discloses iPLA$_2$β and notes on page 9 thereof that "The phospholipase enzyme peptide of the invention ('170 patent) may also be expressed as a product of transgenic animals or prepared by culturing transformed host cells under culture conditions necessary to express the desired phospholipase enzyme peptide desired." Human iPLA2Beta is also discussed in The human calcium-independent phospholipase A2 gene, Multiple enzymes with distinct properties from a single gene, Eur. J. Biochem. 262, 575–585 (1999).

Accelerated phospholipid hydrolysis during myocardial ischemia has been implicated as a biochemical mechanism underlying ischemia-induced ventricular tachyarrhythmias (VT) and sudden death[1-4]. Murine myocardium contains diminutive amounts of calcium-independent phospholipase A$_2$β (iPLA$_2$β) activity (<5% that of human heart[5]) and malignant ventricular tachyarrhythmias are infrequent during acute murine myocardial ischemia[6-7]. This is a major pharmaceutical goal. Accordingly, the inventor discovered that the mouse was a species-specific knockout of the human pathologic phenotype of ischemia-induced lethal ventricular tachyarrhythmias. Left anterior descending artery occlusion of Langendorf-perfused hearts from transgenic mice expressing iPLA$_2$β resulted in the release of fatty acids, the accumulation of lysolipids, and the initiation of malignant ventricular tachyarrhythmias within minutes of ischemia while neither normally perfused transgenic nor ischemic wild-type hearts demonstrated any of these alterations. Moreover, pretreatment of Langendorf perfused hearts from transgenic mice with a phospholipase A$_2$ mechanism-based inhibitor, just minutes prior to the induction of ischemia, completely ablated fatty acid release, lysolipid accumulation, and rescued transgenic hearts from malignant ventricular dysrhythmias. Collectively, these results demonstrate that myocardial ischemia activates iPLA$_2$β in intact myocardium and that iPLA$_2$β-mediated hydrolysis of membrane phospholipids can induce malignant ventricular tachyarrhythmias during acute cardiac ischemia.

The inventor has demonstrated that myocardial ischemia is accompanied by the activation of iPLA$_2$β leading to the release of fatty acids and accumulation of lysolipids in ischemic zones. However, the identity of the phospholipase activated by ischemia was unknown until this invention since it could not be discriminated from the inhibitory profile of racemic BEL alone (BEL inhibits both iPLA$_2$β and iPLA$_2$γ as well as other potential serine lipases not yet identified in myocardium). The proof of the identity of the importance of iPLA$_2$β is now established through the inventor having exploited a species selective knockdown in the mouse of an important pharmaceutical target (human ventricular arrhythmias), reintroduction of the ischemia-induced release of FA and arrhythmias by cardiac myocyte specific expression of the iPLA$_2$β gene, and finally ablation of the ischemia induced arrhythmias through mechanism based inhibition by BEL. Clearly for the first time, the results identify iPLA$_2$β and it endogenous regulatory network as a pharmaceutical target of ventricular arrhythmias for the first time herein. This is not straight forward due to the multiple phospholipases present in ischemic myocardium. Moreover, the invention demonstrates for the first time that the majority of iPLA$_2$β activity in heart tissue is latent and is expressed only after one or more ischemia-induced factors interact with iPLA$_2$β regulatory networks. Thus, the inventor has identified a way to screen for new pharmacologic targets. Although the phenomenology was known, the molecular (pharmaceutical targets) and the direction of future research remained unknown until this invention was discovered.

Moreover, the deliberate overexpression of iPLA$_2$β increases infarct size which can be reduced with BEL treatment. Thus the discovery clearly for the first time defines a evidences iPLA$_2$β as a pharmacologic target in any aspect of phospholipase work by discriminating iPLA$_2$β activity from other phospholipases by the traditional pharmacologic criteria of knockdown, inhibition and rescue by inhibition of the species-specific knock down pathophysiology. The evidence is this proof of concept thereby formally provides an intact, functional organ model to test the effect of pharmacologic agents on ischemia induced arrhythmias by inhibition of iPLA$_2$β regulatory networks. Collectively, this invention and the evidence demonstrates the causative role of iPLA$_2$β in ischemic arrhythmias, demonstrates that ischemia activates iPLA$_2$β leading to accumulation of lysolipids and acylcarnitines thereby providing a novel molecular mechanism for acyl carnitine accumulation in myocardium and sudden death. Collectively, the inventor discovered herein a seminal discovery in that it defines and evidences for the first time in molecular detail a protein target, iPLA$_2$β, for prevention and treatment of ventricular arrhythmias in ischemic zones and identifies a new way to screen for additional targets.

In another aspect, for the first time, the inventor demonstrates and evidences the association of iPLA$_2$β with calmodulin in intact tissue. Previous results in invitro systems identified the increase in activity of iPLA$_2$β in isolated fractions. However this invention demonstrates and is evidence that expressed iPLA$_2$ mass is largely latent until activation by one or more factors in the ischemic process. This discovery is surprising since increased amounts of iPLA$_2$ expression in virtually every system previously studied were suggested to result in increased activity and biologic effects. Here, the inventor discovered that in intact myocardium, in an intact functioning organ model, that the most important factor in accelerated phospholipolysis is the association state of iPLA$_2$ with its regulatory network (e.g. kinases, calmodulin acylcarnitine, etc.).

Further, the inventor discovered that interactions between the recombinant iPLA$_2$β enzyme and such endogenous regulators occur in intact myocardium and demonstrate that it is not only the amount of iPLA$_2$β mass present or latent enzyme activity present but the importance of regulatory events such as the aforedescribed calmodulin-iPLA$_2$β interactions in intact tissue. Since multiple phospholipases are present in heart and since the inventor discovered that iPLA$_2$β activity is largely regulated by networked interactions and not by the amount of mass alone, it was previously impossible to ascribe the release of FA during ischemia and the profibrillatory effects of ischemia to any one of the previously described myocardial phospholipases.

Figure 2B:
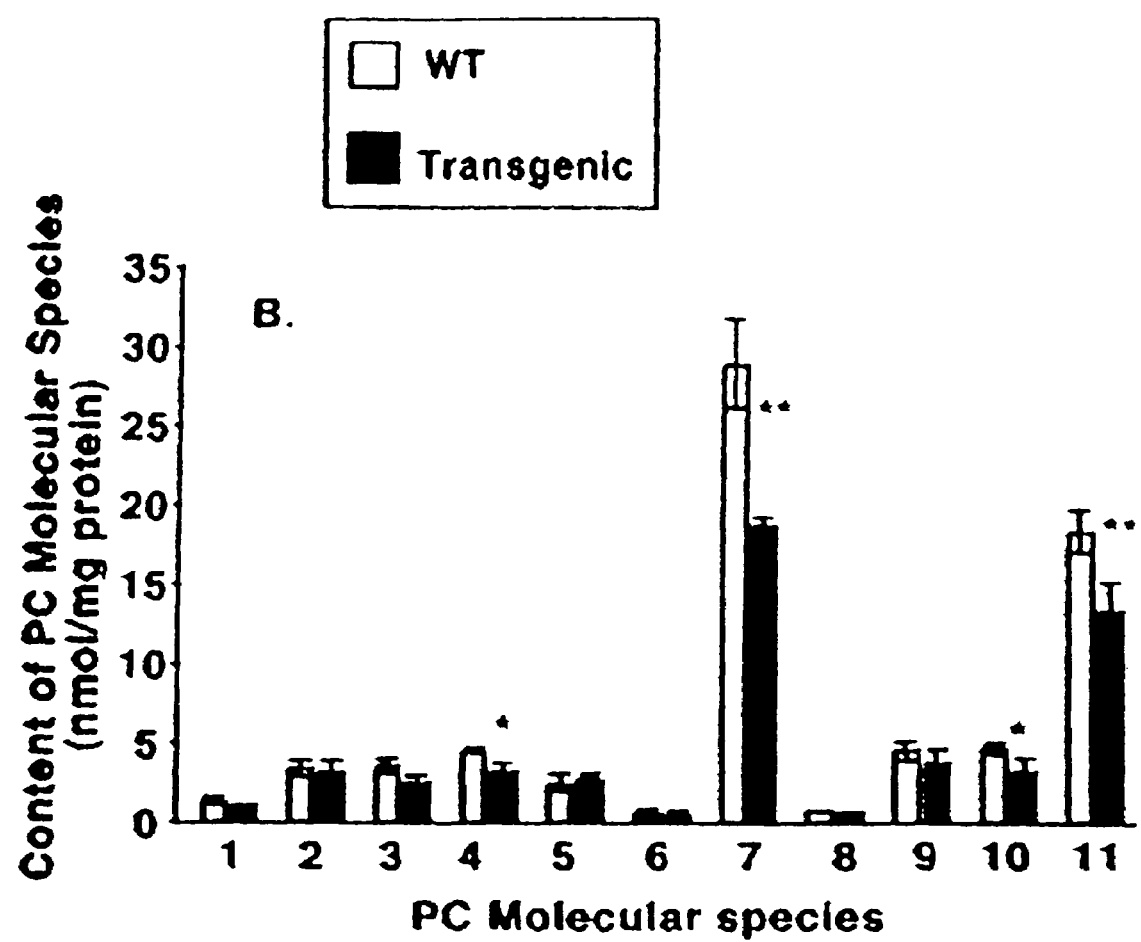

Transgenic mice expressing iPLA$_2$β in a cardiac myocyte function were generated by exploiting the specific inherency in the αMHC promoter. Tissue samples from the major organs of wild-type and transgenic mice (TGiPLA$_2$β) revealed the presence of an intense band corresponding to iPLA$_2$β at the expected molecular mass (80 kDa) in transgenic hearts which was not visible in wild-type heart tissue (FIG. 1a). No expression was detected in brain or liver while a faint band corresponding to iPLA$_2$β was detected in the kidneys of transgenic mice. Both cytosolic and crude membrane fractions from the myocardium of TGiPLA$_2$β mice displayed robust iPLA$_2$β catalytic activity (i.e. 0.6 nmol·min$^{-1}$·mg$^{-1}$ protein in cytosol and 0.1 nmol·min$^{-1}$·mg$^{-1}$ protein in membranes) while cardiac iPLA$_2$β activity was diminutive in wild-type mice (i.e. 0.003 nmol·min$^{-1}$·mg$^{-1}$ protein in cytosol and 0.001 nmol·min$^{-1}$·mg$^{-1}$ protein in membranes). It should be noted that the amount of iPLA$_2$β activity present in transgenic mice is comparable to that naturally present in rabbit[1,4], canine[9,11], and human myocardium[5,17]. No differences in cardiac function were detected by echocardiographic analysis of 4 month old animals nor were any differences in the body weights of littermates, heart weights or in the gross appearance of hearts present. Phospholipid molecular species analysis by electrospray ionization mass spectrometry (ESI/MS) demonstrated modest but statistically significant decreases in some species of choline and ethanolamine glycerophospholipids (FIGS. 2b and c). In each case, other molecular species representing <2% of the total pools were also identified without demonstrable differences between control and transgenic mice. No significant alterations in cardiac anionic phospholipids or in sphingomyelin mass and molecular species content between WT and TGiPLA$_2$β hearts were present.

Figure 4B:
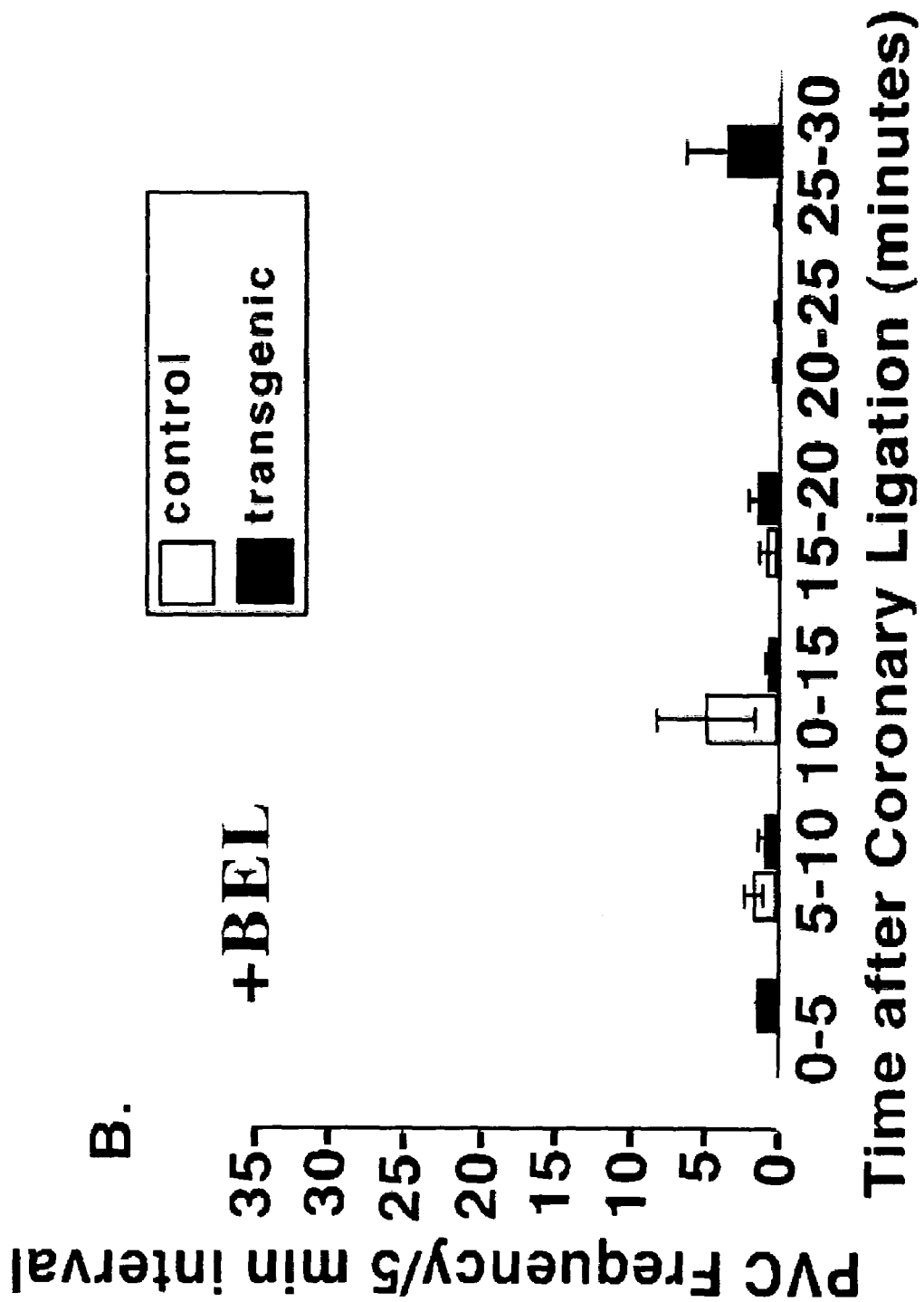
Figure 4C:
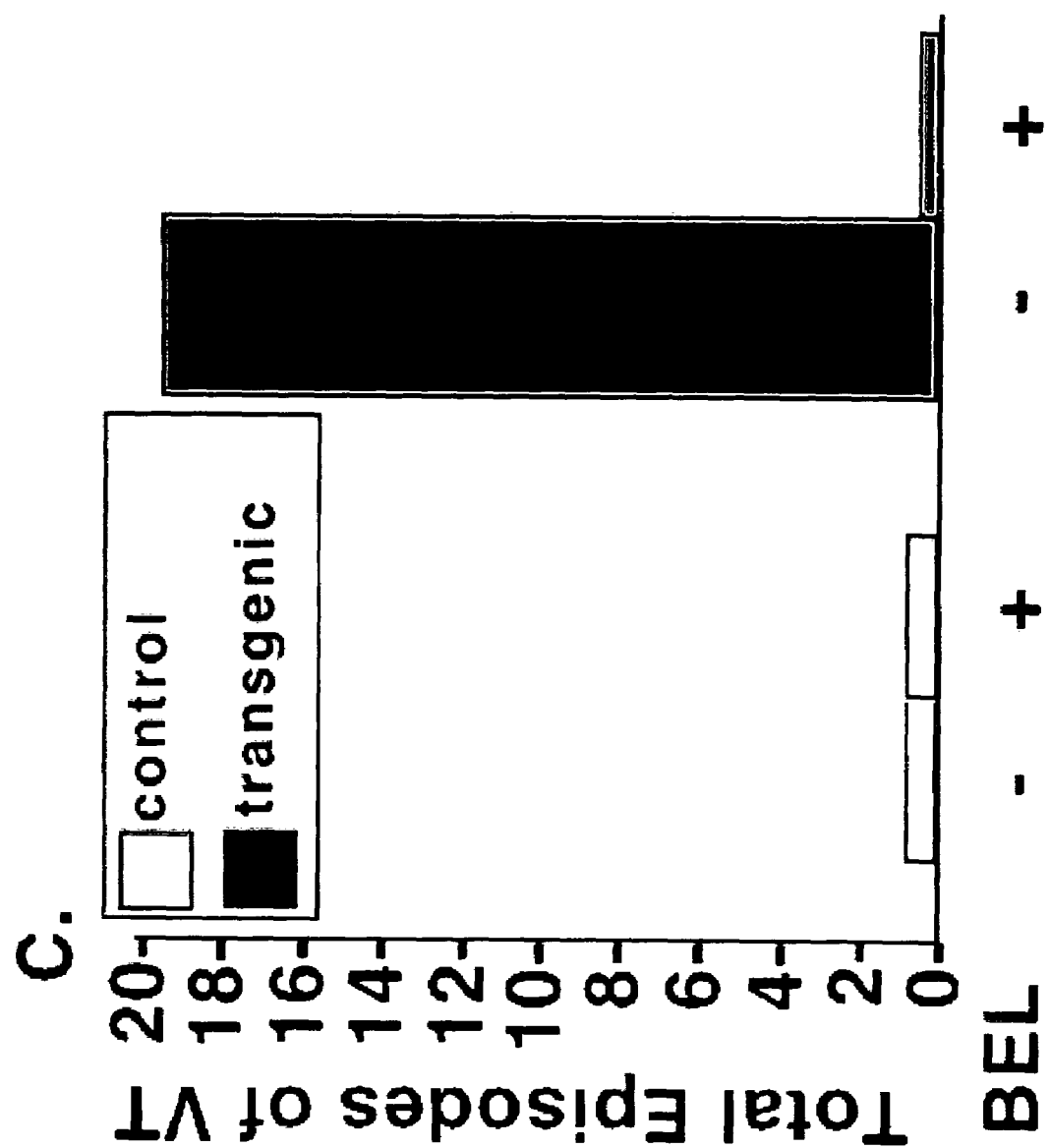

To determine the role of iPLA$_2$β in arrhythmogenesis during acute cardiac ischemia, a Langendorf perfused heart preparation was employed[6]. Ligation of the left anterior descending coronary artery (LAD) in hearts from TGi-PLA$_2$β mice resulted in an increased frequency of premature ventricular contractions (PVCs) and couplets within minutes of cardiac ischemia which was accompanied by malignant ventricular tachyarrhythmias (VT). The frequency of spontaneous PVCs was higher in hearts expressing iPLA$_2$β compared with controls at each 5 minute time interval examined during 30 minutes of ischemia (p=0.0003 vs WT by MANOVA) (FIG. 4). Multiple episodes of non-sustained VT occurred in TGiPLA$_2$β hearts (9 of 24 hearts) compared with a single episode in one WT heart (1 of 19 hearts) (p=0.002). To determine if specific pharmacologic inhibition of the expressed iPLA$_2$β transgene could rescue perfused hearts from transgenic animals from malignant ventricular arrhythmias, the highly selective mechanism based inhibitor (E)-6-(bromomethylene)-3-(1-naphthalenyl)-2H-tetrahydropyran-2-one (BEL)[18] was employed. Pretreatment of Langendorf perfused hearts with BEL (10 μM) just prior to the induction of ischemia inhibited the frequency of PVCs in both TGiPLA$_2$β hearts (P=0.002) and in WT control hearts (p=0.03) (FIG. 4b). Moreover, BEL pretreatment completely abolished VT in TGiPLA$_2$β Langendorf perfused hearts (0/10 (FIG. 4c)).

To determine if ischemia activates iPLA$_2$β catalyzed hydrolysis of lipids in intact myocardium, ESI/MS (electrospray—mass spectrometry) was utilized to quantify the release of fatty acids into the effluent and the accumulation of fatty acids and lysolipids in ischemic zones[19,20]. After 15 min of LAD occlusion, increased release of fatty acids was present in the effluents from perfused hearts and both fatty acids and lysolipids accumulated in the ischemic zone of hearts from TG iPLA$_2$β mice but not WT mice (FIG. 3a). Moreover, the release of fatty acids and accumulation of lysolipids in ischemic zones of hearts from transgenic mice was nearly completely ablated by pretreatment of Langendorf perfused hearts with the iPLA$_2$β mechanism-based inhibitor BEL (FIG. 3). The concurrent activation of iPLA$_2$β during ischemia in conjunction with the generation of malignant ventricular arrhythmias and their rescue by inhibition of the expressed iPLA$_2$β transgene formally fulfills traditional criteria for proof of a cause and effect relationship between two phenomena (i.e., malignant arrhythmias are not present when virtually no iPLA$_2$β activity is present (WT mice) and malignant arrhythmias are manifest during activation of the expressed iPLA$_2$β transgene by ischemia and arrhythmias are ablated by mechanism-based inhibition of expressed iPLA$_2$β enzymic activity).

In humans, and in most animal models of ischemia, ventricular arrhythmias become manifest after 3–15 minutes of ischemia and subside as continued ischemia (>25–30 minutes) results in cell death[7,8]. However, during acute murine ischemia, spontaneous VT occurs infrequently[6,7] in contrast to the 30–60% incidence of malignant ventricular tachyarrhythmias present in most other species after LAD occlusion (e.g. rabbit, rat, pig, dog, human)[6-8,21,22]. In all cases of which the inventor is aware, acute ischemia-induced arrhythmogenesis is accompanied by phospholipolysis (as assessed by release of fatty acids and accumulation of lysolipids). The inventor has exploited the natural species-specific knockout of iPLA$_2$β in the mouse (which does not possess substantial iPLA$_2$β activity and does not release fatty acids or accumulate lysolipids during ischemia) to recapitulate complex ventricular tachyarrhythmias during murine myocardial ischemia by "knocking in" amounts of iPLA$_2$ activity which are naturally present in rat, rabbit, dog, and human myocardium[4,5,10,11]. Moreover, the fact that the observed arrhythmias were due to the catalytic competency of the expressed iPLA$_2$β transgene was substantiated by the rescue of ischemia-induced ventricular tachyarrhythmias in TGiPLA$_2$β ischemic hearts through mechanism-based inhibition by BEL.

Since cardiac electrophysiologic characteristics are dependent on the lipid constituents surrounding ion channels, it seems likely that ischemia induces activation of iPLA$_2$β in a way in which it can effectively access and hydrolyze sarcolemmal phospholipids. Moreover, rescue of malignant ventricular tachyarrhythmias in transgenic animals by BEL pretreatment minutes prior to ischemia, demonstrates that no preexisting abnormality was present in transgenic hearts predisposing to arrhythmogenesis that was not immediately reversible by BEL. The inventor wishes to specifically point out that these experiments do not mean that other factors do not contribute to ischemia-induced arrhythmogenesis, but rather that ischemia-induced activation of iPLA$_2$β-mediated hydrolysis is sufficient to induce ventricular tachyarrhythmias with a time-course, pattern, frequency, and complexity in the ischemic mouse heart which is strikingly similar to that present in humans[7,8]. These studies, in conjunction with the high iPLA$_2$β activity present in human myocardium[5,17], strongly support the notion that iPLA$_2$β mediated hydrolysis is a prominent, and perhaps a major factor, in ventricular electrical dysfunction and sudden death during human myocardial ischemia.

Accordingly, another aspect of the inventor's invention is the identification of iPLA$_2$β, as the enzymic mediator of electrophysiological abnormalities in ischemic myocardium. Thorough utilization of animals harboring the iPLA$_2$β gene expressed in a tissue specific manner, the inventor discovered that iPLA$_2$β is the mediator of electrical alterations in ischemic myocardium. This does not imply that it is the sole mediator of arrhythmias since arrhythmias may occur from mechanical as well as other mechanisms. Test data in control hearts demonstrate that the major portion of acyl carnitine accumulation is BEL inhibitable. Moreover the amplification of the effects in the transgenic animal identify iPLA$_2$β as the enzymic mediator of the effect. Although prior studies have demonstrated the presence of multiple PLA's from different gene products in myocardium this invention identifies an intact functional organ mouse model of ventricular fibrillation. This is important because the mouse heart, in contrast to virtually every other model of ischemia undergoes small amounts of ventricular arrhythmia. Moreover, the mouse is the prototypic model which, in an aspect of the invention, can be used for the definitive identification of the role of other protein regulators (e.g., calmodulin) or other moieties networked to interactions in with iPLA$_2$β promoting the activation of the enzymic mediator (iPLA$_2$β activity) responsible for cardiac sudden death.

The inventor has discovered that iPLA$_2$β activation is required for a large portion of acyl carnitine accumulation and does not result merely from decreased flux of FA through mitochondrial oxidative pathways alone. The identification of the increase in acyl carnitine which is amplified in the transgenic intact mouse model, inhibitable by BEL in the both the wild type and transgenic animals thereby identifies FA accumulation in ischemic myocardium as an active, enzyme-mediated process (i.e., activated by iPLA$_2$ and or other BEL inhibitable lipases) and not the exclusive result of decreased mitochondrial FA throughput alone. Furthermore, the downstream metabolite of FA in myocardium, acyl carnitine likely contributes to the mechanism leading to arrhythmias since Etomoxir (an inhibitor of acyl carnitine) has previously been shown to inhibit arrhythmias in ischemic hearts. Herein, the inventor identifies that a major portion of the formed acylcarnitine results from iPLA$_2$β activation facilitating the provision of fatty acids for acyl carnitine formation.

In an aspect, an intentional insult of ischemia is impacted on a perfused heart. This insult produces a temporary intentional controlled occlusion of one or more arteries feeding blood to the heart tissue to induce ischemia in the perfused rat heart tissue. The ischemia produces a starvation of blood supply and hence a starvation of oxygen to the rat heart tissue. Generally, a comprehensive extended controlled force is applied to one or more arteries normally supplying oxygenated blood to the perfused rat or mouse heart tissue. The circumference force produces a closure in the artery lumen with a resulting decreased blood flow. This force may be temporary and of such time duration as desired. Ischemia may be induced in other suitable tissue such as brain, kidney, limbs, gut, shin, eyes, lungs with similar intentionally inflicted deleterious sequelae or survival resulting from apoptosis or necrosis.

Isolated heart models are useful tools as an intact organ model for physiological and pharmacological studies of heart operation particularly when a direct analysis of the effects of hormones, mediators or drugs on heart operation is desired which requires an intact heart preparation.

In an aspect, one makes an invitro preparation of an intact heart such as of a rat, rabbit or mouse heart. Normally, the heart (myocardium tissue) is isolated from a body and is perfused at a pressure and under effective perfusion conditions such that the perfused heart is beating on its own power although, optionally, a heart pace maker may be employed if desired to assist in such beating. The perfused heart is able to provide clinically detectable physiological values of measurable heart dynamic parameters including but not limited heart output power including cardiac output, output pressure and ventricle work. Hopefully, the heart model shows its somewhat normal steady state after the passage of a satisfactory time from the induction of intentional perfusion. This places the heart model in a satisfactory state to receive administration of the drug.

In an aspect, the intact heart is hung or suspended on a satisfactory mechanical holding device for ready viewing and measuring of the heart's dynamic operation. In an aspect, the administration of a drug is carried out in a manner which is satisfactory to capably deliver the drug to the perfused heart. The amount of drug so delivered is that amount which is reasonably thought to be capable of being received by the perfused heart and responded thereof is such heart is at least responsive a drug.

At least one of the heart tissue and venous eluent from the heart can be examined for metabolic alterations or altered lipid homeostasis by ESI mass spectrometry (acylcarnitines, lysolipids, ceramides free fatty acids as previously described).

As used herein, the term "acylcarnitine" includes acylcarnitine as described in Reference for acylcarnitine, Ford, Han & Gross, Biochemistry 35 (1996), 7903–7909 Reference for lysoPC and ceramide: Han, Analytical Biochemistry 302 (2002), 199–212 and Han & Gross, Journal of Lipid Research 44 (2003), 1071–1079 Acylcarnitine includes carnitine compounds and derivatives thereof which are the condensation product of a carboxylic acid and carnitine including the transport form for a fatty acid crossing the mitochondrial membrane. As used herein the term "carnitine" includes naturally occurring hydrophilic amino acid derivatives.

As used herein, the term "lysolipid" includes monoalkyl, alkenyl and acyl lysolipids including lysolecithin. As used herein lysolipid includes derivatives such as "lysolipid analogs" which are characterized in U.S. Pat. No. 6,602,861 which issued to Charles Pidgeon et al on Aug. 5, 2003 as containing the fatty acid 12MO bonded to the sn-1 position and hydrogen bonded at the sn-2 position of the glycerol backbone. Alternatively, the lysolipid analogs may contain the heteroatom fatty acid, (e.g., 12MO) bonded to the sn-2 position and the hydrogen bonded to the sn-1 position including the D- and L-stereoisomers.

As used herein the term "ceramide" includes N acyl sphingosine, the lipid moiety of glycosphingolipids. As used herein, the term "Glycosphingolipids (GSLs) includes amphipathic compounds consisting of sugar and ceramide moieties, are ubiquitous components of the plasma membrane of all vertebrate cells. As used herein, the term "ceramide' includes derivatives thereof.

In an aspect, an analysis for ceramide is carried out by mass spectrometry for ESI analysis as previously described.

An effective amount of induced myocardial ischemia is that amount of restriction of oxygenated blood flow to a myocardial tissue wherein the absence of an inhibitor of $iPLA_2\beta$ induces malignant ventricular arrhythmia on the transgenic model.

As used herein, an effective amount of inhibitor to the expression of $iPLA_2\beta$ is that amount of inhibitor which when present blocks or prevents the expression of $iPLA_2\beta$ in ischemia induced myocardial tissue.

Typically, herein, an animal model comprises tissue subjectable to ischemia and when so subjected to ischemia expresses $iPLA_2\beta$. In an aspect, the animal model comprises a living animal. In an aspect the living animal is a living mammal such as a murine. In an aspect, the living mammal is a mouse of the wild type, a transgenic mouse or a knockout mouse. In an aspect the animal model comprises living mammalian tissue. In an aspect the term "subjectable" means that the tissue will diligently respond to a restriction in oxygenated blood flow to the tissue with ischemia symptomatology.

In an aspect the transgenic animal model is prepared and the putative drug is administered to the animal model in an amount deemed to be an effective amount. Further, the animal is subjected to ischemia such that in the absence of an inhibitor that the animal would display clinically detectable manifestations of malignant ventricular arrhythmia.

In an aspect, a transgenic mouse is generation by utilizing a myocyte specific expression of $iPLA_2\beta$ using an effective promoter such as an alpha MHC promoter. The transgenic mouse is then subjected to the receipt of an inhibitor effective amount of a putative inhibitor of $iPLA_2\beta$ and the amount of expressed $iPLA_2\beta$ protein mass or $iPLA_2\beta$ activity is measured. In an aspect, if the amount of $iPLA_2\beta$ mass or activity expressed is greater than, equal to, or substantially the same as the amount of $iPLA_2\beta$ expressed by the transgenic mouse in the absence of any administration of any $iPLA_2\beta$ inhibitor, then the putative candidate inhibitor is determined to be an inhibitor of $iPLA_2\beta$.

As used herein, the term "putative" means thought or deemed, supposed, reputed to be an inhibitor of the expression of $iPLA_2\beta$ mass or activity in myocardial tissue.

As used herein the term "tissue" include tissue and collections of a multiplicity of cells. In an aspect, the tissue is living mammalian tissue.

Advantageously, transgenic mice are used to provide intact heart models. Thus, one can study them for gene function or regulation and as for knockout mice human disease. The transgenic mouse provides a system of added function in the event of expression of a new protein. There can be a loss of function in the event there is an adverse interference with the expression of a gene such as an interruption. Again it is necessary to introduce DNA into the cells of the early mouse embryo that contributes to the germ line.

There are several ways to make transgenic mice. In one way called pronuclear microinjection, the foreign DNA is introduced directly into the mouse egg just after fertilization. Using a needle the DNA is injected into the large male pronucleus which is derived from the sperm. The DNA tends to integrate as many tandemly arranged copies to a random position in the genome, often after one or two cell divisions have occurred. Thus the resulting mouse is only partially transgenic. If the transgenic cells contribute to the germ line, then the next generation of mice will be fully transgenic.

In another method the introduction of DNA into embryonic stem cells which are derived from very early mouse embryo and which have the capability to differentiate into all types of cells when introduced into another embryo.

Various methods of making transgenic mice are disclosed in (a) methods in Molecular Biology, Volume 29, Transgenic Mouse Methods and Protocols, Edited by Marten H. Hofkw and Jan van Deusen, Humana Press, Totona, N.J. 2003, both of which are incorporated herein in their entirety by reference.

While the principal advantages and features of the invention have been explained herein, a fuller understanding and appreciation for the invention may be obtained by referring to the drawings and description which follow which are not intended to be limiting.

The following specific examples illustrating the best currently-known method of practicing this invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description. In the following examples, which illustrate the invention, and throughout the specification, parts and percent are by weight unless otherwise indicated.

EXAMPLES

Methods

Generation of Transgenic Mice. Overexpressing iPLA$_2$β in a cardiac myocyte specific manner. Cardiac myocyte specific expression of iPLA$_2$β in transgenic mice was achieved using the αMHC promoter[16]. Briefly, the 2.4 kb coding region of the wild-type Chinese hamster iPLA$_2$β gene was cloned downstream of the αMHC promoter, linearized with NotI, and the DNA was microinjected directly into the pronuclei of pseudopregnant mouse (B6CBAF1/J) zygotes. Pups were screened for the presence of the transgene by tail PCR analysis. Founders that were positive for the transgene were mated with nontransgenic animals (C57B1/J6, Jackson Laboratories, Bar Harbor, Me.) to establish transgenic lines. Second and third generation heterozygous mice, typically 3–4 months of age were used for all studies.

Homogenization and Western Analysis of Control and Transgenic Mouse Hearts. For preparation of cytosolic fractions, samples of tissue were homogenized in 25 mM imidazole, pH 8.0, containing 1 mM EGTA and 0.25 M sucrose utilizing a Polytron tissue homogenizer, centrifuged at 100,000×g for 1 h and the pelleted membrane fraction was resuspended in a volume of homogenization buffer equal to the cytosolic fraction (supernatant). Proteins were separated by SDS PAGE[23] and transferred to polyvinylidene difluoride membranes for probing with antibodies directed against iPLA$_2$β peptide corresponding to residues 277–295 (CS-QIHSKDPRYGASPLHWAK)[24] in conjunction with a protein A-horseradish peroxidase conjugate. Recombinant iPLA$_2$β used as a standard was prepared as previously described[25].

Assay of Calcium-Independent Phospholipase A$_2$ Activity. Assays were performed with tissue homogenates or subcellular fractions (100–300 µg protein) incubated in 100 mM Tris-HCl, pH 7.0, containing 4 mM EGTA in the presence of L-α-1-palmitoyl-2-[1-$^{14}$C]-arachidonyl-phosphatidylcholine (5 µM final concentration) (NEN) at 37° C. for 5 minutes essentially as previously described[25].

Electrospray Ionization Mass Spectrometry of Lipids from Wild type and Transgenic Mouse Myocardium. Lipids were extracted from mouse myocardium (~50 mg) by a modified Bligh and Dyer technique utilizing 50 mM LiCl in the aqueous layer in the presence of internal standards selected based on their lack of demonstrable endogenous molecular ions in that region[19,20]. ESI/MS analysis was performed utilizing a Finnigan TSQ-7000 Spectrometer as previously described[19,20].

Isolated perfused mouse heart preparations were utilized as previously referenced (1). Briefly, a traditionally accepted ex vivo intact model of acute ischemia was studied. The left anterior descending (LAD) coronary artery was occluded in isolated perfused hearts. Mice were anesthetized with sodium pentobarbital (150 mg/kg IP), and their hearts were rapidly excised and placed in oxygenated Krebs-Henseleit buffer containing (in mmol/L): NaCl 118.3, KCl 2.7, MgSO4 1.0, KH2PO4 1.4, NaHCO3 29.0, CaCl2 3.4, and glucose 10, plus insulin 70 mU/L and BSA 2.8%, at 37° C. Hearts were perfused by retrograde aortic flow with oxygenated buffer at 37° C. Flow rates were adjusted to maintain constant perfusion pressures of 45 to 50 mm Hg. Hearts were simultaneously superfused in a bath containing oxygenated buffer at 37° C. to maintain constant temperature.(1) Circulation 101:547–552 (2000).

Ischemic Studies with Isolated Langendorf-Perfused Mouse Hearts. Ventricular tachyarrhythmias induced by acute ischemia were characterized with use of an isolated, Langendorf-perfused heart preparation as described previously by Lerner et al[6] which is incorporated herein in its entirety by reference. Frequencies of spontaneous arrhythmias (PVCs, and episodes of VT) were counted for 30 min after coronary ligation and tablulated as PVC frequency per 5 minute intervals. A run of ventricular tachycardia was defined as 10 or more beats with a cycle length <100 msec. After 30 min, hearts were perfused through the aortic catheter with 1% Evans blue dye. To determine the effects of BEL on induction of arrhythmias after ischemia, hearts were perfused with buffer containing 10 µM BEL beginning 5 min before coronary ligation and during ischemia. All studies were randomized and blinded.

In an aspect, ischemia studies are carried out using an isolated rat or mouse beating heart following the procedure outline at http://adinstruments.com/research/rapps/langendorff.html which is incorporated herein in its entirety by reference.

Statistical Analyses. Data (presented as means±s.e.m.) were subjected to MANOVA analysis and two tailed Student's t tests and regarded as significant at P<0.05.

The abbreviations used are PLA$_2$, BEL (E)-6-(bromomethylene)-3-(-naphthalenyl)-2H-tetrahydropyran-2-one; ESI/MS, electrospray ionization mass spectrometry; MS/MS, tandem MS; PVC, premature ventricular contraction; VT, ventricular tachyarrhythmias; LAD, left anterior descending; TGiPLA$_2$β, transgenic iPLA$_2$β, transgenic iPLA$_2$β, aMHC, a myosin heavy chain; ANOVA, analysis of variance; cPLA$_2$, cytosolic phospholipase A$_2$; WT, wild-type.

In recent years a large number of combinatorial and other enhanced chemistry techniques have been developed which now allow large multimillion compound libraries of diverse compounds to be rapidly synthesized. Such techniques have the potential to greatly accelerate the discovery of compounds which have biologically useful therapeutic properties by providing large assemblies or collections of such diverse chemical compounds for biological screening. The capability to produce such large numbers of compounds for screening is a driver for new methods of screening which are not adversely effected by time and resource constraints. This produces a need for new screening methods and animal models to permit rapid screening of vast compound libraries.

Our human population is experiencing a rapid dramatic increase in diabetes, hypertension and obesity. Diabetes is a chronic disease that affects as many as 16 million Americans. In this situation people having diabetes are unable to use glucose in their food for energy and thus glucose accumulates in their bloodstream wherein it can damage the heart, kidneys, eyes and nerves. Many persons suffer from hypertension which is a state or condition of having a higher than normal arterial blood pressure. Hypertension is an extremely common comorbidity of diabetes affecting about 20–60% of individuals with diabetes. These also are dramatic drivers for the long felt and increasing need to develop new methods and models for rapid screening of compound libraries such as is provided herein.

In an aspect a "safe and effective amount" of a compound identified as an anti-arrhythmia and using this discovery is an amount that is effective, to decrease risk of malignant ventricular arrhythmia in a living animal, including a mammal, including a human subject, without undue adverse side effects (such as toxicity, irritation, or allergic response).

The therapeutic or pharmaceutical compositions of the present invention can be administered by any suitable route known in the art including for example intravenous, subcutaneous, intramuscular, transdennal, intrathecal or intracerebral. Administration can be either rapid as by injection or over a period of time as by slow infusion or administration of slow release formulation.

The compositions are usually employed in the form of pharmaceutical preparations. Such preparations are made in a manner well known in the pharmaceutical art. In an aspect, one preparation utilizes a vehicle of physiological saline solution or, but it is contemplated that other pharmaceutically acceptable carriers such as physiological concentrations of other non-toxic salts, five percent aqueous glucose solution, sterile water may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

In an aspect, a specific dose is calculated according to the approximate body weight or body surface area of the patient or the volume of body space to be occupied. The dose will also be calculated dependent upon the particular route of administration selected. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In a number of circumstances, it would be desirable to determine the levels of containing iPLA$_2$β in a patient sample. The term "detection" as used herein in the context of detecting the presence of iPLA$_2$β in a patient is intended to include determining the amount of iPLA$_2$β or the ability to express an amount of iPLA$_{2γ}$ activity in a patient, the distinguishing of iPLA$_2$β from other phospholipases A$_2$, the estimation of prognosis in terms of probable outcome of a degenerative disease and prospect for recovery, the monitoring of iPLA$_2$β levels over a period of time as a measure of status of the condition, and the monitoring of iPLA$_2$β activity or mass levels for determining a preferred therapeutic regimen for the patient.

To detect the presence of iPLA$_2$β in a patient, a sample is obtained from the patient. The sample can be a tissue biopsy sample from a heart or a sample of blood, plasma, serum, CSF (cerebral spinal fluid) or the like. To detect the presence of iPLA$_2$β, an enzymatic analysis or Western blot analysis can be performed.

In an aspect, the invention comprises a method for screening a compound library to determine the relative or absolute therapeutic capability of a compound to pharmacologically effectively inhibit ischemia induced activation of iPLA$_2$β in an intact myocardium comprises treating an intact myocardium with a compound from library, intentionally inducing ischemia in the myocardium tissue and determining the level of expression of iPLA$_2$β activity, assess the functional status of the iPLA$_2$β regulator network in an intact organ, the results of changes in flow or work on the activity of iPLA$_2$β activity and thereby to identify endogenous modulators of that network demonstrating novel pharmaceutical targets therefrom.

References

1. Gross, R. W. & Sobel, B. E. Augmentation of cardiac phospholipase activity induced with negative liposomes. Trans. Assoc. Am. Physicians 92, 136–147 (1979).

2. Gross, R W. & Sobel B E. Arrhythmogenic amphiphilic lipids and the myocardial cell membrane. J. Mol. & Cell. Card. 14, 619–626, 1982

3. Gross, R. W. Myocardial phospholipases A$_2$ and their membrane substrates. Trends in Cardiovascular Medicine. 2, 115–121 (1992).

4. Ford D. A. Alterations in myocardial lipid metabolism during myocardial ischemia and reperfusion. Progress in Lipid Research. 41, 6–26 (2002).

5. Hazen, S. L. & Gross, R. W. Identification and characterization of human myocardial phospholipase A$_2$ from transplant recipients suffering from end stage ischemic heart disease. Circ. Res. 70, 486–495 (1992).

6. Lerner D. L., Yamada K. A., Schuessler R B. & Saffitz J E. Accelerated onset and increased incidence of ventricular arrhythmias induced by ischemia in Cx43-deficient mice. Circulation 101, 547–552 (2000).

7. London B. Cardiac arrhythmias: from (transgenic) mice to men. J. Cardiovasc. Electrophysiol. 12, 1089–1091 (2001).

8. Braunwald E, Zipes, D. P. & Libby, P. eds. Heart Disease: A Textbook of Cardiovascular Medicine. (W. B. Saunders Company, Philadelphia 2001).

9. Wolf, R. A. and Gross, R. W. Identification of neutral active phospholipase C which hydrolyzes choline glycerophospholipids and plasmalogen selective phospholipase A$_2$ in canine myocardium J. Biol. Chem. 260, 7295–7303 (1985).

10. Hazen, S. L. Stuppy, R. J. & Gross, R. W. Purification and characterization of canine myocardial cytosolic phospholipase A$_2$: A calcium independent phospholipase with absolute sn-2 regio specificity for diradyl glycerophospholipids. J. Biol. Chem. 265, 10622–10630 (1990).

11. Hazen, S. L. & Gross, R. W. The specific association of a phosphofructokinase isoform with myocardial calcium-independent phospholipase A$_2$: Implications for the coordinated regulation of phospholipolysis and glycolysis. J. Biol. Chem. 268, 9892–9900 (1993).

12. Ordway, R. W., Walsh, J. V., Jr. & Singer, J. J. Arachidonic acid and other fatty acids directly activate potassium channels in smooth muscle cells. Science 244, 1176–1179 (1989).

13. Gubitosi-Klug, R., Yu, S. P., Choi, D. W. & Gross, R. W. Concomitant acceleration of the activation and inactivation kinetics of the human delayed rectifier K+ channel (Kv1.1) by Ca2+-independent phospholipase A$_2$. J. Biol. Chem. 270, 2885–2888 (1995).

14. Stewart, A., Ghosh, M., Spencer, D. M., and Leslie, C. C. Enzymatic properties of human cytosolic phospholipase A$_{2γ}$. J. Biol. Chem. 277, 29526–29536 (2002).

15. Mancuso, D. J., Jenkins, C. M. & Gross, R. W. The genomic organization, complete mRNA sequence, cloning, and expression of a novel human intracellular membrane-associated calcium-independent phospholipase A$_2$. J. Biol. Chem. 275, 9937–9945 (2000).

16. Robbins, J, Subramaniam, A & Glick J. A multipurpose vector for the study of transcriptional control. Gene 85, 541–544 (1989).

17. Hazen, S. L. & Gross, R. W. Human myocardial cytosolic calcium-independent phospholipase A$_2$ is modulated by ATP:Concordant ATP-induced alterations in enzyme kinetics and mechanism-based inhibition. Biochem. J. 280, 581–587 (1991).

18. Zupan, L. A., Weiss, R. H., Hazen, S. L., Parnas, B. L., Aston, K. W., Lennon, R. J., Getman, D. P. & Gross, R. W. Structural determinants of haloenol lactone-mediated suicide inhibition of canine myocardial calcium-independent phospholpase $A_2$. J. Med. Chem. 36, 95–100 (1993).

19. Han, X. & Gross, R. W. Electrospray ionization mass spectroscopic analysis of human erythrocyte plasma membrane phospholipids. Proc. Natl. Acad. Sci. USA 91, 10635–10639 (1994).

20. Han, X., Gubitosi-Klug, R. A., Collins, B. J. & Gross, R. W. Alterations in individual molecular species of human platelet phospholipids during thrombin stimulation: Electrospray ionization mass spectrometry-facilitated identification of the boundary conditions for the magnitude and selectivity of thrombin-induced platelet phospholipid hydrolysis. Biochemistry 35, 5822–5832 (1996).

21. Wit, A. L. & Janse, M. J. Experimental models of ventricular tachycardia and fibrillation caused by ischemia and infarction. Circulation 85, I32–I41 (1992).

22. Wit, A. L. Janse, M. J. The ventricular arrhythmias of ischaemia and infarction. Electrophysiological mechanisms. (Futura Publishing, Mount Kisco N.Y. 1993).

23. Janse, M. J., Opthof, T., & Kléber, A. G. Animal models of cardiac arrhythmias. Cardiovasc. Res. 39, 165–177 (1998).

24. Laemmli, U. K. Cleavage of structural proteins during the assembly of the head of bacteriophage T4. Nature 227, 680–685 (1970).

25. Jenkins, C. M., Wolf, M. J., Mancuso, D. J. & Gross, R. W. Identification of the calmodulin-binding domain of recombinant calcium-independent phospholipase $A_2\beta$: Implications for structure and function. J. Biol. Chem. 276, 7129–7135 (2001).

26. Wolf, M. J. & Gross, R. W. Expression, purification, and kinetic characterization of a recombinant 80-kDa intracellular calcium-independent phospholipase $A_2$. J. Biol. Chem. 271, 30879–30885 (1996).

As used herein, the term "administration" includes the administering of the effective amount of a compound to a recipient in a manner, in an amount and under delivery condition which are intended to illicit a response to that administration whereby any influence or impact of the presence o the drug in the recipient can be detected and whereby the drug is presented to the recipient in a manner whereby the functional effect of the drug may be manifested if there is a functional effect.

Useful nonlimiting pharmaceutical formulation components includes sugar, cellulose, starch, emulsifier, wetting agent, antioxidant, preservatives, stabilizers and phosphate buffer solutions. If the administration is by injection then the pharmaceutical carrier is likely sterile and optionally with a blood compatible agent with a pH adjusted to recipient blood system pH. It is desired that the administration be of benefit to the recipient of the administration. Components of the administration, dosage, method of delivery will be selected so as to provide medicinal benefit to the recipient of the administration.

In an aspect, compositions would be provided in unit dosage form which is an amount which is medically acceptable and suitable for delivery to the recipient such as a living human of an ani-arrhythmia drug.

The composition may be administered in a variety of forms such as oral, rectal, topical, nasal, ocular, peroral, sublingual, buccal, suppository or parenteral administration and optionally in a pharmaceutically acceptable formulation. The administration selected will be chosen on the basis of a number of factors including the efficacy of delivery and delivery speed to the patient in a manner befitting the medical situation urging the administration of the anti-arrhythmia drug.

In an aspect, an anti-arrhythmia drug can be targeted to a location with a recipients body by using targeting ligands. If, for example, delivery is desired to ischemic cardiac tissue, the compound to be delivery is coupled or ligand to a cardiac cell marker. If desired, the anti-arrhythmia drug is coupled or conjugated to an antibody or fragment thereof which is immunoreactive with a cardiac cell marker. The antibody or ligand is selected so that it is suitable for reacting or recognizing the intended target tissue.

In an aspect, of using a perfused animal model such as a perfused mouse heart, one can add compounds to perfusate determine the effects first on FA release, then induce ischemia and measure FA release, arrhythmias and infarct size. If desired, the compounds are administered to the intact animal model in the perfusate in the Langendorf or in intact animals IV. Generally, it is preferable to have knockout or knockdown mice. If desired, one can reintroduce enzyme to determine effect, then after effects are documented block by treatment with BEL. Activation of $iPLA_2\beta$ is also important in other diseases such as brain ischemia, other ischemic syndromes, and insulin release such as in diabetes. The perfused heart is common and use of perfusion and effluents in Langendorf hearts tissue retrograde through the aorta is common; each has its own documentation previously and has been done in many variations in brain, kidney, fat tissue, skeletal muscle, smooth muscle amongst other perfusion systems.

In an aspect, a method of TAG analysis and lipid analysis useful in this invention is carried out by using a method disclosed in U.S. patent application U.S. Ser. No. 10/606, 601 filed Jun. 26, 2003, "Spectrometric Quantitation of Triglyceride Molecular Species" which is incorporated herein by reference in its entirety. A level of expression greater or less than expression in an absence of the substance selected to be measured indicates and is determinant of activity in modulating $iPLA_{2\epsilon}$expression.

In a first embodiment, in regard to the method of analysis disclosed in U.S. Ser. No. 10/606,601, a method for the determination of TG individual (i.e. separate) molecular species in a composition of matter such as the above in a biological sample comprises subjecting a biological sample to lipid extraction to obtain a lipid extract and subjecting the lipid extract to electrospray ionization tandem mass spectrometry (ESI/MS/MS) providing TG molecular species composition as a useful output determination.

In an aspect, the inventive concept comprises analyzing a biological sample using electrospray ionization tandem mass spectrometry (ESI/MS/MS) and performing a two dimensional analysis with cross peak contour analysis on the output of the ESI/MS/MS to provide a fingerprint triglyceride individual (i.e. separate) molecular species.

Briefly, the inventive methods present a novel two-dimensional approach/method which quantitates individual molecular species of triglycerides by two dimensional electrospray ionization mass spectroscopy with neutral loss scanning. This method is also useful for polar lipid analysis by ESI/MS using conditions as outlined in U.S. Ser. No. 10/606,601 (see above) and is protected by a provisional patent and be reference herein. This method provides a facile way to fingerprint each patient's (or biologic samples) triglyceride composition of matter (individual molecular species content) and lipid composition of matter directly from chloroform extracts of biologic samples. Through selective ionization and subsequent deconvolution of 2D intercept density contours of the pseudomolecular parent ions and their neutral loss products, the individual molecular species of triglycerides and phospholipids can be determined directly from chloroform extracts of biological material. This 2D (two dimensional) approach comprises a novel enhanced successful functional therapy model for the automated determination and global fingerprinting of each patient's serum or cellular triglyceride and phospholipid profile content thus providing the facile determination of detailed aspects of lipid metabolism underlying disease states and their response to diet, exercise or drug therapy.

In an aspect of this inventive method, tandem mass spectroscopic separation of specific lipid class-reagent ion pairs is used in conjunction with contour density deconvolution of cross peaks resulting from neutral losses of aliphatic chains to determine the individual triglyceride molecular species from a biological sample (blood, liver, muscle, feces, urine, tissue biopsy, or rat myocardium).

In an aspect, a biological sample from an animal model is processed in tandem mass spectrometer a first mass spectrometer set up in a tandem arrangement with another mass spectrometer. In that regard the biological sample can be considered as sorted and weighed in the first mass spectrometer, then broken into parts in an inter-mass spectrometer collision cell, and a part or parts of the biological sample are thereafter sorted and weighed in the second mass spectrometer thereby providing a mass spectrometric output readily and directly useable from the tandem mass spectrometer.

In an aspect, a pre-analysis separation comprises a separation of lipoproteins prior to lipid extraction. In an aspect, the pre-analysis separation comprises at least one operation or process which is useful to provide an enhanced biological sample to the electrospray ionization tandem mass spectrometry (ESI/MS/MS). In an aspect, a pre-analysis separation is performed on a biological sample and two compositions are prepared accordingly from the biological sample. In an aspect one composition comprises high density lipoproteins and another composition comprises low density lipoproteins and variants thereof comprised of intermediate densities which can, if necessary, be resolved by chromatographic or other density techniques.

Generally, a biological sample taken is representative of the subject from which or of which the sample is taken so that an analysis of the sample is representative of the subject. In an aspect a representative number of samples are taken and analyzed of a subject such that a recognized and accepted statistical analysis indicates that the analytic results are statistically valid. Typically the composition is aqueous based and contains proteinaceous matter along with triglycerides. For example, a human blood sample is sometimes used. Through use of this inventive method, a plasma sample can be analyzed and appropriate information from the plasma can be extracted in a few minutes. Alternatively, information can be taken from the cells in the blood as well.

In an aspect, serum is utilized as a biological sample. After whole blood is removed from a human body and the blood clots outside the body, blood cells and some of the proteins become solid leaving a residual liquid which is serum.

In an aspect a control sample is employed in the analysis.

In an aspect, the biological sample or a representative aliquot or portion thereof is subjected to lipid extraction to obtain a lipid extract suitable for ESI/MS/MS. In an aspect lipids are extracted from the sample which in an aspect contains a tissue matrix. Non-lipid contaminants should be removed from the lipid extract.

While the invention has been described in terms of various specific embodiments, those skilled in the art will recognize that the invention can be practiced with modification within the spirit and scope of the claims.

What is claimed is:

1. A method for evaluating a compound to determine the therapeutic capability of the compound to pharmacologically inhibit ischemia induced activation of calcium independent phospholipase ($iPLA_2$) in an intact tissue which comprises treating a tissue model with a candidate compound, inducing ischemia in the tissue and determining if there has been a change in the expression of $iPLA_2$ activity as a result of networked interactions between $iPLA_2\beta$ and an $iPLA_2$ regulatory network.

2. A method in accordance with claim 1, wherein a determination is made that the compound is an anti-arrhythmic compound when there has been a reduction in $iPLA_2$ activity.

3. A method in accordance with claim 1 which further comprises analyzing for the presence of fatty acids in the tissue or venous effluent (or other markers of $iPLA_2$ activity such as lysolipids or acylcarnitines) and if fatty acids are absent or notably reduced from an induction of ischemia when compared to that in a nontreated tissue, determining that the compound is an inhibitor of $iPLA_2$.

4. A method in accordance with claim 2 wherein the determination of the compound inhibited ischemia induced activation of $iPLA_2$ comprises at least one of using ESI/MS to quantify the release of fatty acids into the effluent of the tissue and measuring the accumulation of fatty acids and lysolipids in ischemic zones of the tissue.

5. A method in accordance with claim 1, wherein said method further comprising measuring the amount of at least one free fatty acid, acylcarnitine, lysolipid and ceramide in a living system or the tissue during control or ischemic conditions and if the amount of at least one of free fatty acid, acylcarnitine, lysolipid and ceramide is the greater, the same as or lesser than the compounding normal amount then determining that the tonic inhibition is modified i.e. is a drug which is a potential anti-arrhythmia drug or an agent which decreases infarction size or aneuryism formation.

6. A method in accordance with claim 1, wherein said method further comprises measuring or determining the molar or weight ratio of one compound to another and if the ratio is greater than control less than or equal to ischemic values then the inventor determines that the test compound is a drug which is an anti-arrhythmic drug based on an analysis therein.

7. A method in accordance with claim 1, wherein said method further comprises determining that the compound inhibited the ischemia activation of $iPLA_2$, in an isolated perfused heart model and using ESI/MS to quantify the release of fatty acids into the effluent and measuring the accumulation of fatty acids and lysolipids in ischemic zones of the heart model.

8. A method in accordance with claim 1 wherein the tissue is an intact myocardium.

* * * * *